(12) United States Patent
Taniguchi

(10) Patent No.: US 7,167,579 B2
(45) Date of Patent: Jan. 23, 2007

(54) METHOD AND APPARATUS FOR DETERMINING THE SEX OF A FERTILIZED EGG

(75) Inventor: Ryosuke Taniguchi, Nagasaki-ken (JP)

(73) Assignees: Kabusiki Kaisya Horiuchi, Kurume (JP); Towa Sangyo Kabusiki Kaisya, Nohgata (JP)

( * ) Notice: Subject to any disclaimer, the term of this patent is extended or adjusted under 35 U.S.C. 154(b) by 661 days.

(21) Appl. No.: 10/232,180

(22) Filed: Aug. 30, 2002

(65) Prior Publication Data

US 2003/0185422 A1    Oct. 2, 2003

(30) Foreign Application Priority Data

Mar. 27, 2002    (JP) ............... 2002-088135

(51) Int. Cl.
*G06K 9/00* (2006.01)
*A01K 43/04* (2006.01)
*A01K 37/00* (2006.01)

(52) U.S. Cl. ............... 382/110; 209/510; 119/713
(58) Field of Classification Search ............... 382/110
See application file for complete search history.

(56) References Cited

U.S. PATENT DOCUMENTS 3,153,288 A    10/1964    Abel 6,029,080 A * 2/2000 Reynnells et al. .......... 600/407
6,506,570 B1 * 1/2003 Phelps ...................... 435/7.21

FOREIGN PATENT DOCUMENTS

| DE | 10 21 623     |   | 12/1957 |
|----|---------------|---|---------|
| EP | 1 118 267     |   | 7/2001  |
| FR | 2 738 638     |   | 3/1997  |
| GB | 457543        |   | 3/1936  |
| JP | 61234798 A    | * | 10/1986 |
| JP | 01055131 A    | * | 3/1989  |
| JP | 06153742 A    | * | 6/1994  |
| JP | 2001-238559 A |   | 9/2001  |
| JP | 2002253085 A  | * | 9/2002  |
| WO | WO 00 01302   |   | 1/2000  |

\* cited by examiner

*Primary Examiner*—Bhavesh M. Mehta
*Assistant Examiner*—Utpal Shah
(74) *Attorney, Agent, or Firm*—Frishauf, Holtz, Goodman & Chick, P.C.

(57) ABSTRACT

An accuracy of the sex determination which is visually inspected by human based on a reference drawing of an egg shape prepared for every parent chicken is insufficient and it takes much time to perform such a determination. Thus, the sex of the fertilized egg is determined by using parameters representing features developed on a surface shape of the above described fertilized egg which are quantified based on contour image data of the above described fertilized egg obtained by taking an image of the fertilized egg which is placed on a setting stand.

32 Claims, 20 Drawing Sheets

F I G. 3
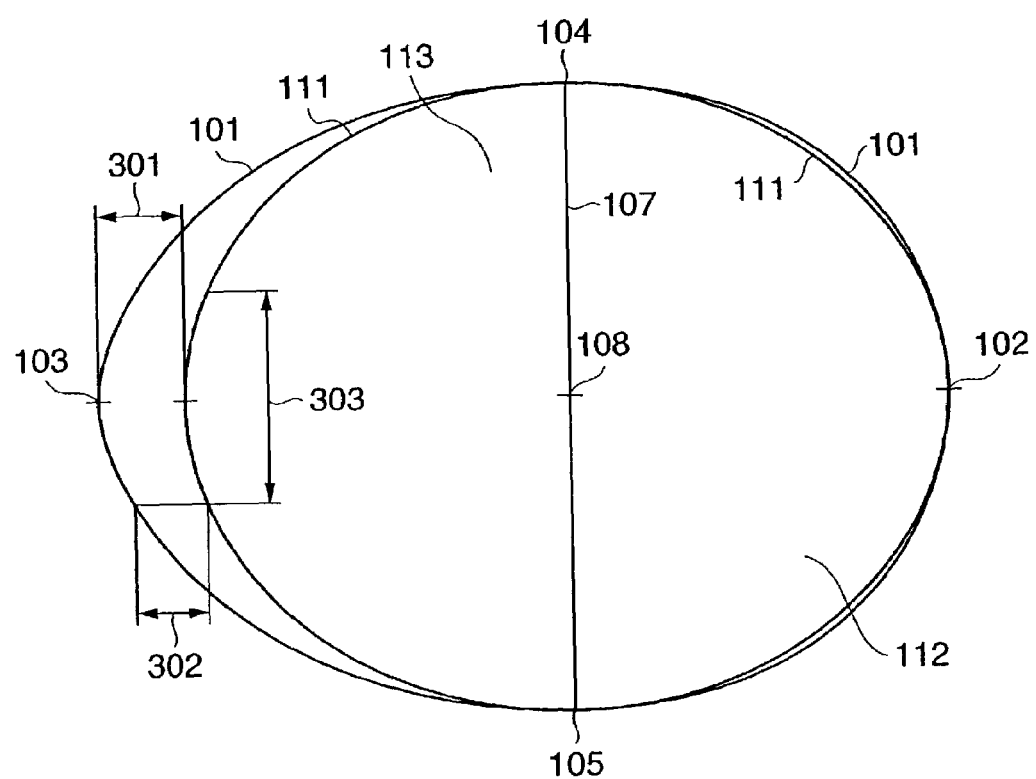

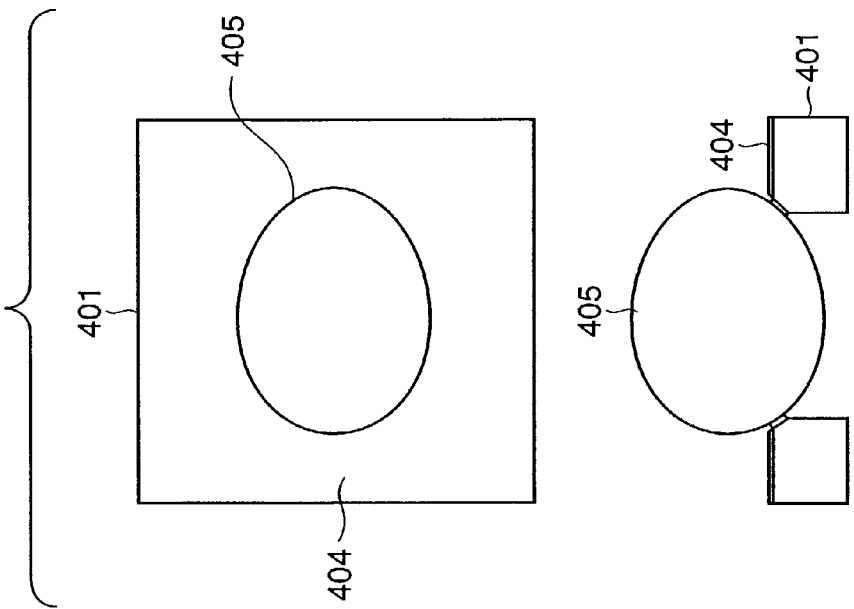
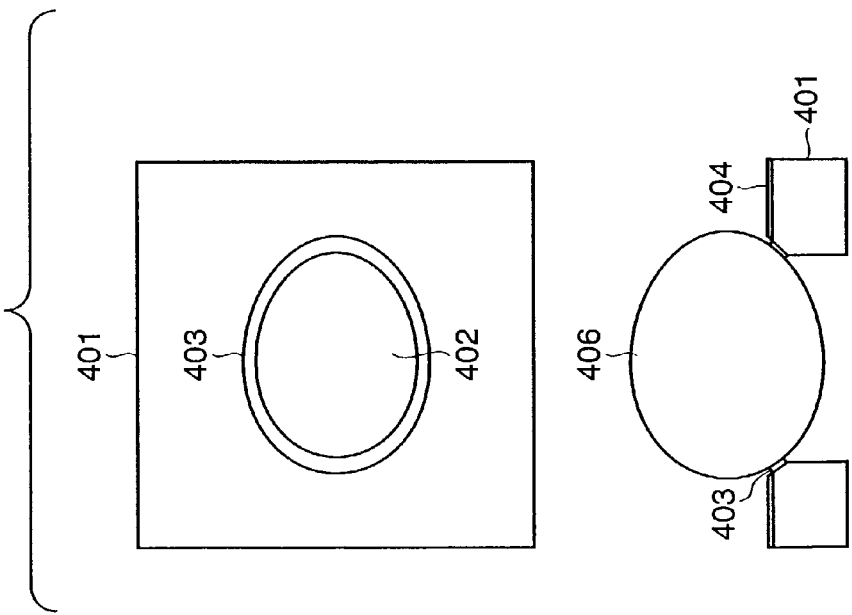

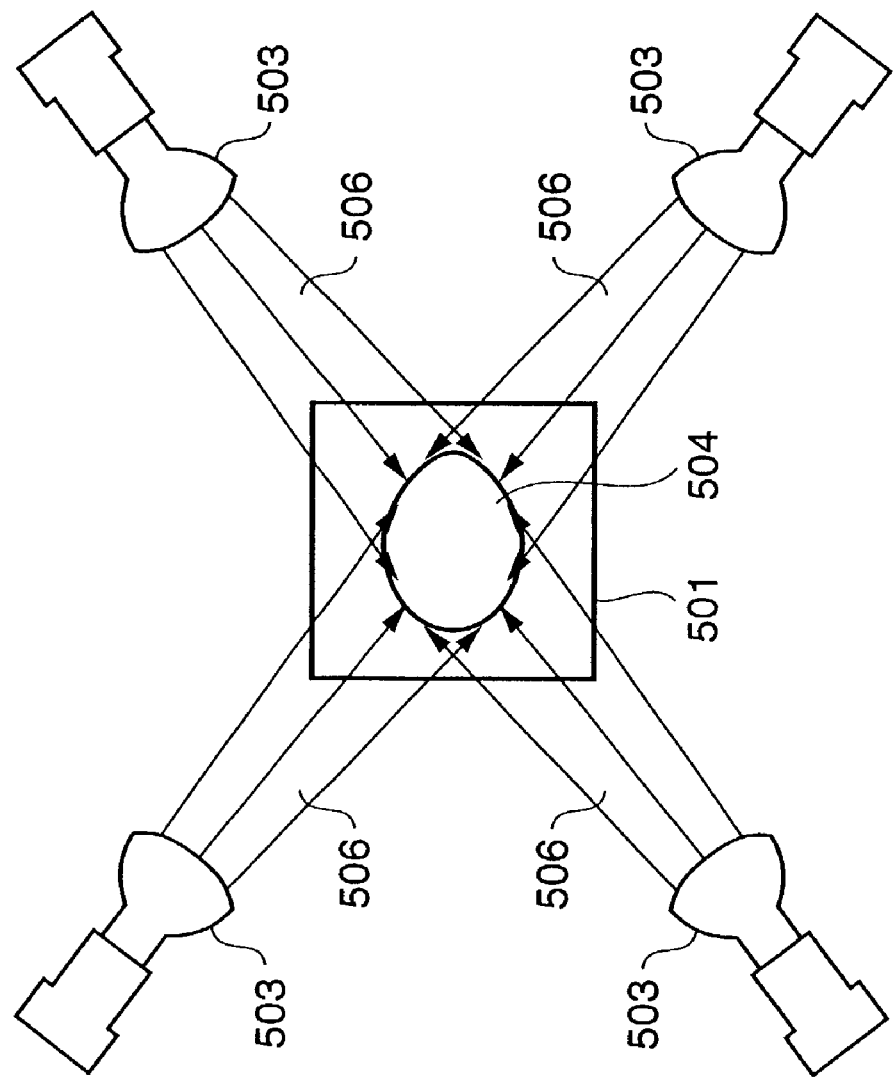

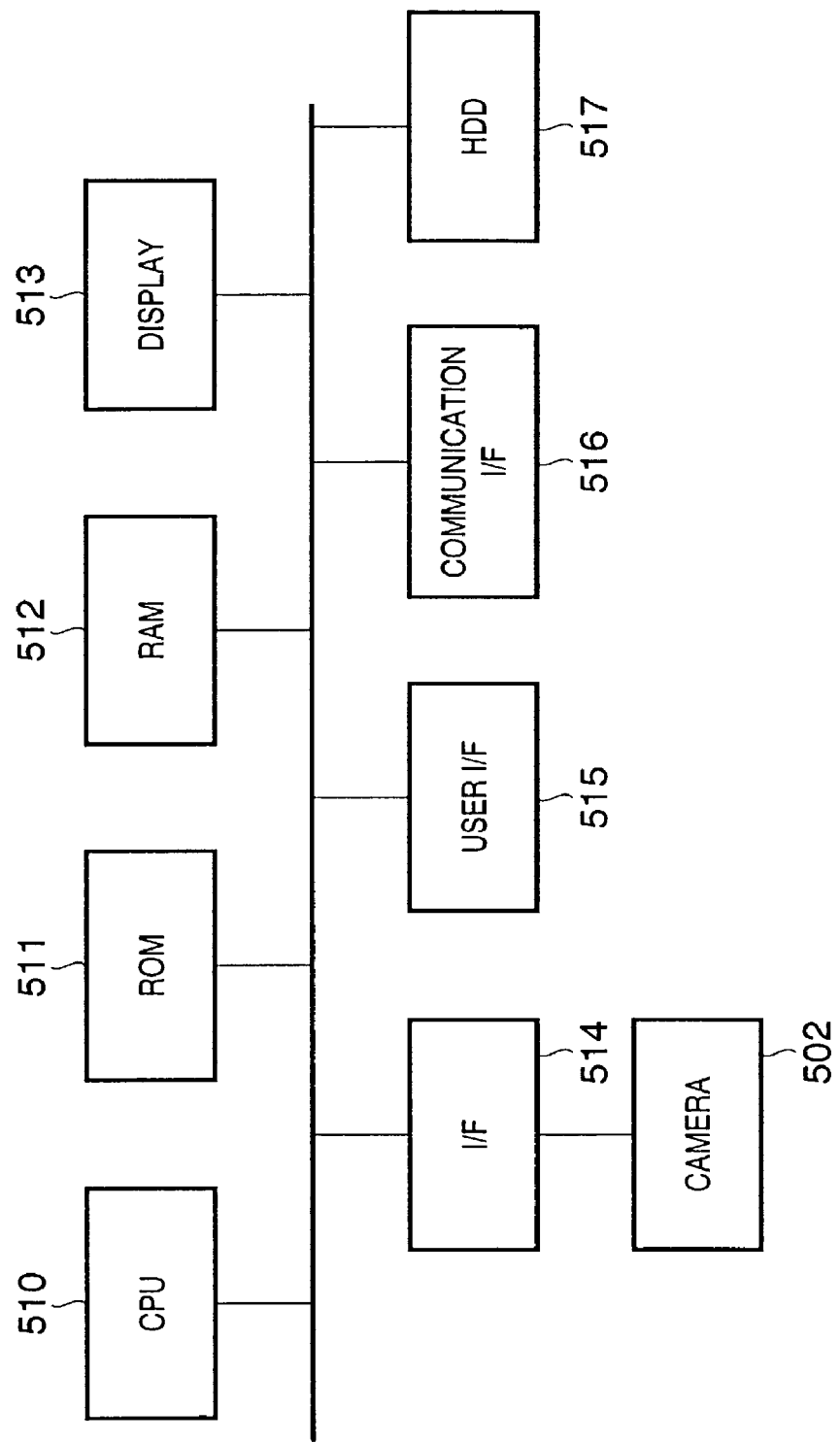

FIG. 18

| G-No | YR90 | R85 | Gym | L85 | GPT | GYR90 | R50BX | DFH | GR | DSY |
|------|------|-----|-----|-----|-----|-------|-------|-----|-----|-----|
| 1 | | | | | | | | | | |
| 2 | | | | | | | | | | |
| 3 | | | ○ | | | | | | | |
| 4 | | ○ | | | ○ | | | | | |
| 5 | ○ | | | | ○ | | | | | |
| 6 | ○ | | | | | | | | | |
| 7 | ○ | ○ | ○ | ○ | ○ | | | | | |
| 8 | | | | | | | | | | |
| 9 | | | | | | | | | | |
| 10 | | | ○ | | | | | | | |
| 11 | | | | ○ | | | | | | |
| 12 | ○ | ○ | | | | | | | | |
| 13 | | | ○ | | | | | | | |
| 14 | | | | | | | | | | |
| 15 | | | | | | | | | | |
| 16 | | | | ○ | ○ | | | | | |
| 17 | | | | | | | | | | |
| 18 | | | ○ | ○ | | | | | | |
| 19 | | | ○ | | | | | | | |
| 20 | | ○ | | | | | | | | |
| 21 | | | ○ | | | | | | | |
| 22 | | | ○ | | | | | | | |
| 23 | | | ○ | | | | | | | |
| 24 | ○ | ○ | | | | | | | | |
| 25 | | | | | | | ○ | | | |
| 26 | | | | | | ○ | | | | ○ |
| 27 | | | | | | ○ | ○ | | | |
| 28 | | | | | | | ○ | | | |
| 29 | | | | | | ○ | | | | |
| 30 | | | | | | | | ○ | | ○ |
| 31 | | | | | | ○ | | | | ○ |
| 32 | | | | | | | | | | ○ |
| 33 | | | | | | | ○ | | | |
| 34 | | | | | | ○ | | | | |
| 35 | | | | | | | | ○ | | ○ |
| 36 | | | | | | | | | | ○ |
| 37 | | | | | | | ○ | | | |
| 38 | | | | | | | | | ○ | ○ |
| 39 | | | | | | | ○ | | | |

METHOD AND APPARATUS FOR DETERMINING THE SEX OF A FERTILIZED EGG

FIELD OF THE INVENTION

The present invention relates to a method and an apparatus for determining the sex of a fertilized chicken egg, and more particularly, to a method and an apparatus for determining the sex of a fertilized chicken egg by using parameters representing features developed on a surface shape of the described fertilized egg which are quantified based on contour image data of the described fertilized eggs.

BACKGROUND OF THE INVENTION

Among birds such as chickens, which include varieties raised mainly for their eggs such as the White Leghorn, only the egg-producing females are useful. By contrast, among chickens raised for their meat, both the males and the females are useful, although males and females mature at different rates and it is therefore more efficient to raise them separately. In the case of both types of the above-described varieties of chickens, for these and other reasons the chicks are sexed 2–3 days after they are hatched in order to determine what sex they are.

Three methods are currently used to determine the sex of the hatchlings: (a) by hand, (b) by machine or (c) by utilizing sex-controlled inheritance (that is, sex-linked inheritance) characteristics.

All three of the above-described conventional methods involve sexing a hatched chick, so unless the egg is hatched the sex of the chick to be hatched cannot be determined. As a result, in the case of the White Leghorn chickens raised to produce eggs, for example, the time and expense of hatching eggs containing male chicks is wasted. In addition, in the case of such egg-producing varieties of chickens, those chicks found to be male are destroyed, which is undesirable from the viewpoint that life in all its forms should be respected.

If it were possible to reliably sex the chicks before they are hatched, that is, while still in the egg, the above-described wastage and dilemma could be avoided. Prior to hatching, for example, the males could be used for food or for the production of vaccines.

A method for determining the sex of a fertilized chicken egg, based on a shape of the egg, has been practiced for a long time in Kyushu or in Southeast Asia. In this method, references are established respectively for a male egg and a female egg for every parent chicken, primarily in terms of a shape of a wide side of the egg (a blunt end side having an airspace), that is, a bulge of the wide side of the egg. Then, an egg within the reference range has been found to be a female egg or a male egg.

In addition, a method for comparing shapes of blunt end portions (that is, end portions having larger diameters and roundness) of various chicken eggs has also been used. In this technique, a profile projector is used to take a blown-up profile of the laid egg for each hen, after which the eggs are allowed to hatch, the hatchlings are sexed, and the shapes of the eggs are categorized according to the sex of the resulting chick. This process is repeated over a certain period of time until a reference range is established for each hen, after which reference profiles are produced. Thereafter, the shape of a laid egg to be sexed is then compared to the reference profiles in order to determine the sex of the unhatched chick.

However, the above-described conventional chicken egg sexing technique has the following drawbacks.

(a) It is commercially impractical to get reference profiles for each hen, because a lot of chickens are bred in the poultry farming business.

(b) The technique relies on the human eye to compare the blunt end of the egg to be sexed against the reference profile established for that hen, and as such is not entirely reliable.

(c) The work of producing the reference profiles for sexing the eggs involves the above-described steps, so it is a relatively lengthy process.

(d) Eggs (especially, fertilized eggs) available in recent years having a conventional shape such that a wide side of the egg is bulged and a narrow side of the egg is narrower than the wide side have gradually decreased, whereas round eggs, or eggs whose maximum bulge portions are positioned at the center of thereof, or elongated eggs have increased. Thus, the shape of the egg is very complicated, so that it is difficult to determine the sex in regard to all of the eggs consistently according to only a part of the references of the egg shape. Therefore, it becomes difficult to determine the sex with high accuracy. In addition, the determination of the sex based upon only the bulge or roundness of the wide side is insufficient to definitely classify the eggs into males and females and leads to errors.

Therefore, in the method for determining the sex based upon the egg shape as in the past, it is difficult to perform the determination with high accuracy.

SUMMARY OF THE INVENTION

In view of the above described problems, the present invention provides a method, a program, and an apparatus for determining the sex of a fertilized egg with high accuracy and at a high speed without influence of the varieties of parent chickens which lay the fertilized egg and variations in shapes of the fertilized egg.

In the above described method, program, and apparatus for determining the sex which are provided by the present invention, the sex of the fertilized egg is determined based upon basic features (specifically, a bulge of a wide side of the egg, roundness or sharpness at a blunt end of the egg, a bulge, roundness or sharpness of a narrow side of the egg, a bulge of the entire fertilized egg, a center, a figgy shape peculiar to the fertilized egg, for example) for determining the sex of the fertilized egg, the basic features being extracted from image data of a contour of the fertilized egg. The above described basic features can be quantified as parameters which are extractable based upon the whole contour of the fertilized egg or as a combination of the above described parameters. Also, the above described basic features can be quantified by utilizing not only a contour of the fertilized egg in itself but also an approximated ellipse of the contour of the fertilized egg which depends on a shape characteristic of an individual fertilized egg to recognize a bulge or roundness which cannot be found only by a characteristic of the contour line segment. This approximated ellipse can be obtained from a position of a maximum width of the fertilized egg and a blunt end of the fertilized egg.

In addition, it becomes possible to determine the sex without depending on the individual parent chicken by combining a plurality of the above described basic features, so that a rate of determination can be improved.

However, the above described basic features are quantified which are within an extremely narrow numerical range, thus, an accurate whole shape of the fertilized egg and a high-contrast image thereof are required to determine the sex with high accuracy.

The basic features for determining the sex as described above are extracted by hatching the fertilized egg whose image has already been captured, determining the sex of the hatchling by hand, and analyzing a correlation between the sex of the hatchling and the image already captured. Specifically, the whole contour of the egg is extracted from the image from which the whole contour of the fertilized egg can be obtained, a lot of parameters conceivable from the contour data and new parameters obtained by combining the above described parameters are quantified to compare with determination results, and the correlation between the converted parameters and the results is analyzed to extract the features.

That is, using the predetermined parameters obtained from the contour data of the fertilized egg or a combination of the above described parameters, a predetermined feature of the contour of the fertilized egg can be quantified. The features are "a bulge of a wide side" and "a sharpness of a narrow side", for example, and factors of representing such features are parameters such as a length, a width, or an area at an arbitrary position of the contour. Since these parameters and a combination thereof can be quantified based on the contour data of the fertilized egg, the features such as "a bulge of a wide side" described above are numerically expressed based on a shape of the fertilized egg. If the sex determination of the fertilized egg can be performed based on the numerical values obtained herein, a feature such as "a bulge of a wide side" in itself corresponding to the above described numerical value will represent the sex of the fertilized egg. As described above, the basic features are features extractable from the whole contour of the fertilized egg and useful for determining the sex of the fertilized egg.

In order to solve the above described problems with the understanding of the above described matter, the present invention provides a method, an apparatus, and a program for determining the sex of the fertilized egg based on the basic features of the fertilized egg, the basic features becoming a reference for determining the sex of the fertilized egg and being able to be quantified based on the contour data of the fertilized egg extracted from an image from which the whole contour of the fertilized egg can be obtained.

Other objects, features and advantages of the present invention besides those discussed above shall be apparent to those skilled in the art from the description of a preferred embodiment of the invention which follows. In the description, reference is made to accompanying drawings, which form a part thereof, and which illustrate examples of the invention. Such examples, however, are not exhaustive of the various embodiments of the invention, and therefore reference is made to the claims that follow the description for determining the scope of the invention.

BRIEF DESCRIPTION OF THE DRAWINGS

The invention will be better understood and its numerous objects and advantages will become more apparent to those skilled in the art by reference to the following drawings, in conjunction with the accompanying specification, in which:

FIG. 3 is a diagram showing an example of a parameter obtained from a contour of an egg and an approximated ellipse of the egg used for the sex determination according to the present invention;

FIGS. 4A and 4B are diagrams showing a configuration of an egg stand according to the present invention;

FIG. 5B is a diagram showing an example of an arrangement of a lighting fixture 503 in FIG. 5A;

FIG. 5C is a schematic diagram showing a configuration of a computer 505 in FIG. 5A;

FIG. 18 is a list showing a result of determining the sex of 39 eggs by applying a determination processing according to an embodiment of the present invention.

DETAILED DESCRIPTION OF THE PREFERRED EMBODIMENTS

Preferred embodiments of the present invention will be described in detail in accordance with the accompanying drawings.

Figure 1:
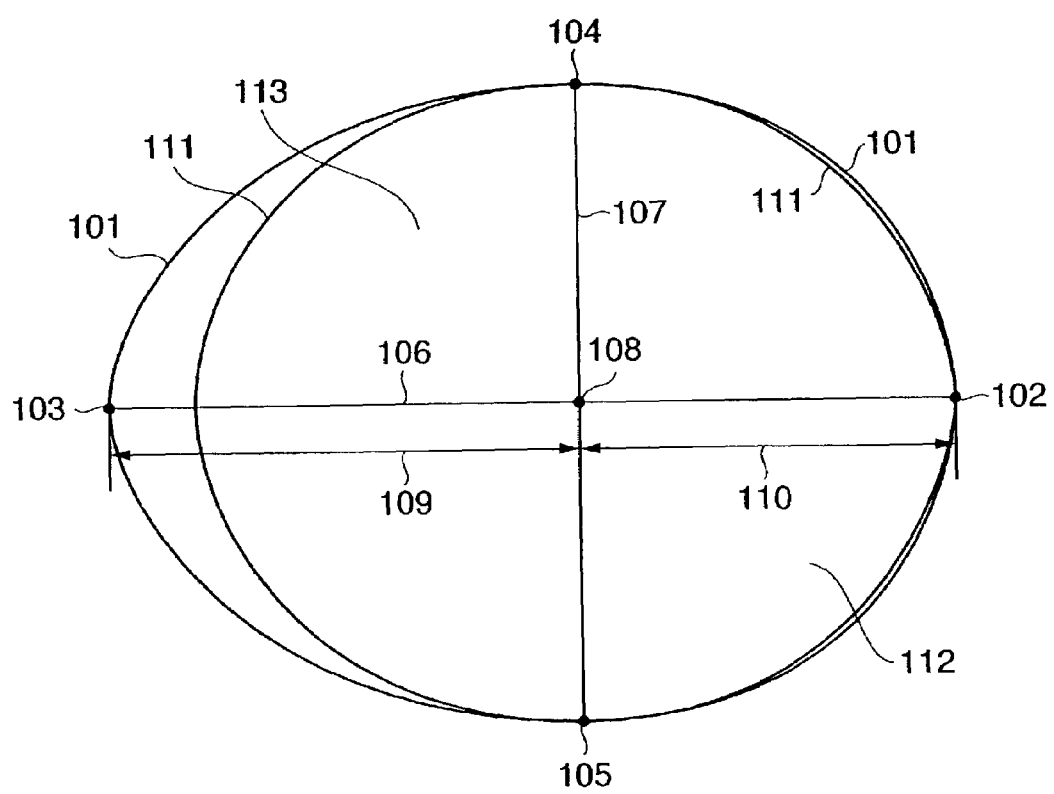
FIG. 1 is a diagram for defining an region within an egg used for the sex determination according to the present invention.

Now, terms and parameters used for embodiments of the present invention will be described below with reference to FIG. 1. And, in the following description, a fertilized egg will be often abbreviated as "an egg" for the sake of simplicity. FIG. 1 shows a whole contour of a fertilized egg as well as a contour of an approximated ellipse centering on a center of the fertilized egg, and a blunt end of the fertilized egg is positioned on the right side of this figure. Reference numerals in this figure represent terms and parameters which are used in this specification. In an image of the fertilized egg, a boundary between the egg and a background of the image is firstly detected, then the detected boundary is arranged as a two-dimensional graphic to produce a graphic 101. This graphic 101 is defined as a contour of the egg.

"A blunt end" refers to a right end 102 which is on a wide side of the contour 101 of the egg having an airspace.

"A narrow end" refers to a left end 103 which is on a narrow side of the contour 101 of the egg without having an airspace.

"An upper end" refers to an uppermost point 104 of the contour 101 of the egg, the point 104 being located on a circumference having a minor axis of the egg.

"A lower end" refers to a lowermost point 105 of the contour 101 of the egg, the point 105 being located on a circumference having a minor axis of the egg.

"A major axis" of the egg refers to a length 106 of a line which is connected between the blunt end 102 and the narrow end 103 of the egg, and a value of the length 106 is represented as Lx.

"A minor axis" of the egg refers to a length 107 of a line which is connected between the upper end 104 and the lower end 105, and a value of the length is represented as Ly.

"A width" of the egg refers to a length of a line which is orthogonal to the major axis 106 and defined by the contour 101 of the egg, and a maximum value of the width of the egg (a maximum width) is Ly.

"A center" refers to a intersection point 108 of two lines, that is, a line which is connected between the blunt end 102 and the narrow end 103 of the egg and a line which is connected between the upper end 104 and the bottom end 105 of the egg.

"A length from a center to a narrow end (a length of a narrow side)" refers to a length 109 of a line which is connected between the narrow end 103 and the center 108, and a value of the length is represented as Lxt.

"A length from a center to a blunt end (a length of wide side)" refers to a length 110 of a line which is connected between the center 108 and the blunt end 102, and a value of the length is represented as Lxh.

"A center-based approximated ellipse (abbreviated as an approximated ellipse, hereinafter)" refers to an ellipse 111 which is illustrated such that the center 108 of the egg is used as a center of the ellipse 111, the length from the center to the blunt end 110 of the egg is used as a long radius of the ellipse 111, and the minor axis 107 of the egg is used as a minor axis of the ellipse 111.

"A wide side" of the egg refers to a right side 112 of a line which is connected between the upper end and the bottom end of the egg, and the "a narrow side" of the egg refers to an opposite side 113 of the line.

"An area" of the egg refers to an area of a portion which is defined by the contour 101 of the egg, and a value of the area is represented as Sx.

"A wide area" of the egg refers to an area of the wide side of the egg, and a value of the wide area is represented as Sxh.

"A narrow area" of the egg refers to an area of the narrow side of the egg, and a value of the narrow area is represented as Sxt.

"An area of an approximated ellipse" refers to an area of a portion which is defined by the contour of the approximated ellipse 111 of the egg, and a value of the area is represented as Sxd.

"A wide area of an approximated ellipse" refers to an area of a wide side of the approximated ellipse, and a value of the wide area is represented as Seh.

"A narrow area of an approximated ellipse" refers to an area of a narrow side of the approximated ellipse, and a value of the narrow area is represented as Set.

[Example of Extracting Features for Determining the Sex]

Basic features which become references for determining the sex will be described below. The purpose for determining the sex of fertilized eggs is that the fertilized eggs are classified into male eggs and female eggs with reliability and the male eggs are prevented from being hatched. However, each of the references used for determining the sex can be required only for determining whether an egg, which meets the reference, among a set of eggs is absolutely female or male. Therefore, it is not necessary that all of the female eggs or male eggs meet the reference. Because there is no perfect reference which can be applied to an egg, a natural product, but the sex can be determined with reliability by simply applying a plurality of the references which meet the above described requirements.

Therefore, each of the basic features described below is not perfect, but such feature can be used to determine the sex of some eggs among a set of female or male eggs with reliability.

<Basic Features of Male>

It can be said that an egg having features as described below has high probability of being as a male egg.

An egg in which a curvature of a contour 101 in the vicinity of a blunt end 102 is small, that is, an egg whose tip portion at a wide side is sharpened.

An egg in which, at its wide side, a width of the egg in the vicinity of a midpoint between a center and a blunt end is large, and more specifically, an egg in which a difference between the width of the egg in the vicinity of the midpoint between the blunt end and the center and a maximum width of the egg is small, that is, an egg whose wide side is too large.

An egg in which, at its narrow side, a width of the egg in the vicinity of a midpoint between a center and a narrow end is large, and more specifically, an egg in which a difference between the width of the egg in the vicinity of the midpoint between the center and the narrow end and a maximum width of the egg is small, that is, an egg whose narrow side is large.

An egg whose width in the vicinity of a narrow end is large, that is, an egg whose tip portion at its narrow side is large.

An egg whose minor axis 107 is short relative to a contour 101 of the egg, that is, an egg having an elongated shape (it can also be said that the egg is like a rugby ball).

<Basic Features of Female>

It can be said that an egg having features as described below has a high probability of being as a female egg.

An egg in which a curvature of a contour 101 in the vicinity of a blunt end 102 is large, that is, an egg whose tip portion at a wide side is round.

An egg in which a curvature of a contour 101 in the vicinity of a narrow end 103 is large, that is, an egg whose tip portion at a narrow side is round.

An egg in which a ratio of a width of a narrow side to a width of a wide side of the egg is small, that is, an egg in which the wide side is larger than the narrow side, or the narrow side is restricted (it can also be said that the egg is like a fig).

An egg in which a ratio of a length from a center to a narrow end to a major axis of the egg is larger, that is, an egg whose center is positioned at a higher level.

An egg in which a ratio of a length from a center to a narrow end to a major axis of the egg is smaller, that is, an egg whose center is positioned at lower level.

In addition, an egg whose area is large, that is, a big egg.

Consequently, the references for determining the sex of the egg can be applied to an embodiment by quantifying the above described basic features by utilizing predetermined parameters. In addition, it has become apparent that the above described references can also be statistically adopted in order to compare with a result obtained by actually hatching the egg.

Figure 2:
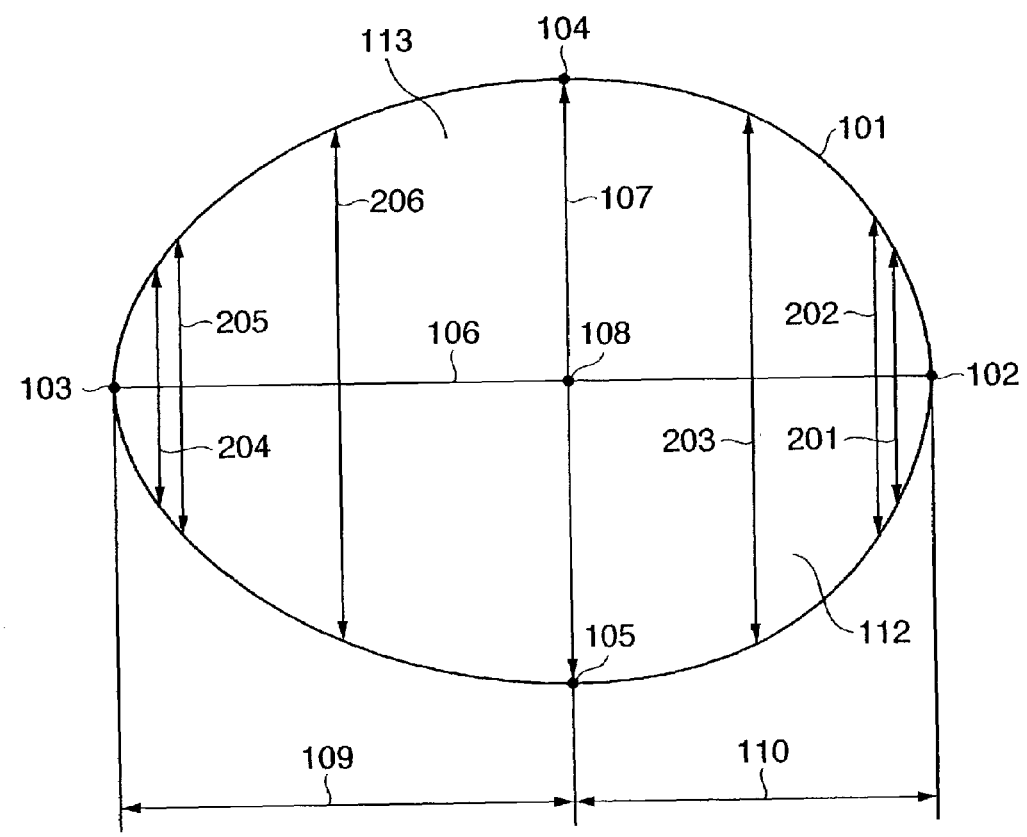
FIG. 2 is a diagram showing an example of a parameter obtained from a contour of an egg used for the sex determination according to the present invention.

Some of the above described basic features for determining the sex can be quantified in association with a width of an egg. Then, FIG. 2 shows examples of parameters associated with widths of an egg used for quantifying the above described basic features for determining the sex. The widths of an egg described herein are set such that they are suitable for representing any of the above described basic features. In addition, like reference numerals are used in FIG. 2 to denote like elements already described in FIG. 1.

A width length 201 refers to a length of a line which intersects at right angle with a line from a center to a blunt end of an egg at a position being 90% of the whole length from the center to the blunt end of the egg when viewed from the center of the egg, and further which is also defined by a contour of the egg. A value of the length 201 is represented as Wh 90.

A width length 202 refers to a length of a line which intersects at right angle with a line from a center to a blunt end of an egg at a position being 85% of the whole length from the center to the blunt end of the egg when viewed from the center of the egg, and further which is also defined by a contour of the egg. A value of the length 202 is represented as Wh 85.

A width length 203 refers to a length of a line which intersects at right angle with a line from a center to a blunt end of an egg at a position being 50% of the whole length from the center to the blunt end of the egg when viewed from the center of the egg, and further which is also defined by a contour of the egg. A value of the length 203 is represented as Wh 50.

A width length 204 refers to a length of a line which intersects at right angle with a line from a center to a narrow end of an egg at a position being 90% of the whole length from the center to the narrow end of the egg when viewed from the center of the egg, and further which is also defined by a contour of the egg. A value of the length 204 is represented as Wt 90.

A width length 205 refers to a length of a line which intersects at right angle with a line from a center to a narrow end of an egg at a position being 85% of the whole length from the center to the narrow end of the egg when viewed from the center of the egg, and further which is also defined by a contour of the egg. A value of the length 205 is represented as Wt 85.

A width length 206 refers to a length of a line which intersects at right angle with a line from a center to a narrow end of an egg at a position being 50% of the whole length from the center to the narrow end of the egg when viewed from the center of the egg, and further which is also defined by a contour of the egg. A value of the length 206 is represented as Wt 50.

Utilizing the above described width lengths 201 (Wh 90) to 206 (Wt 50) in combination with each other, observations on how the width lengths vary at a wide side and at a narrow side can be made. Thus, a bulge of an egg, fatness or slimness of an egg, roundness or sharpness at a blunt end or a narrow end of an egg, or a restriction in a narrow side of an egg can be determined. The way of determining the sex by combining the above described matters based on the basic features of an egg will be described later in detail.

Further, some of the above described basic features of female eggs and male eggs can be quantified in association with an approximated ellipse of the egg. For example, when a contour of a wide side of an egg and its approximated ellipse superimposed thereon are minutely observed, it is found that a contour of the egg matches almost perfectly with a contour of the approximated ellipse, but in some cases, an approximated ellipse extends off the contour of an egg or an approximated ellipse is extremely smaller than an area of an egg. A male hatchling tends to be hatched from such an egg which is largely different from the approximate ellipse. Then, FIG. 3 shows examples of parameters which can be set based on an approximate ellipse and a contour of an egg used for quantifying the above described basic features of female and male eggs. Like reference numerals are used in FIG. 3 to denote like elements already described in FIG. 1.

For example, in order to quantify a basic feature such as "roundness of a tip portion of a wide side", a rate of change of a distance between an contour of an approximated ellipse and a contour of an egg at a narrow side 113 can be adopted. Specifically, given that a distance between a narrow end of the egg and a narrow end of the approximated ellipse is represented as a length 301 and given that a width of the approximated ellipse defined by two lines parallel to the major axis 106, each of which corresponds to a line between a contour of the approximated ellipse and a contour of the egg having a length 302 which is 90% of the length 301 is represented as a width 303, roundness of the tip portion of the narrow side can be determined by the a value of the width 303.

In addition, a basic feature such as "a bulge of a wide side" can be quantified by comparing a contour 101 of the egg with an approximated ellipse 111 at a wide side 112 of the egg. For example, although a contour of the wide side of the egg extremely matches with a contour of the approximated egg, a bulge of the wide side can be determined by obtaining a difference between a wide area of the egg and a wide area of the approximated ellipse at a wide side 112, and also, the bulge of the wide side can be determined by detecting a misalignment between the contour 101 and the approximated ellipse 111 at an arbitrary point of the wide side.

Each of the predetermined parameters for the egg shown in FIG. 2 and FIG. 3 is merely an example of an element which can be used for quantifying the above described basic features, and other parameters can also be extracted without using the above described parameters shown in these figures, as long as the above described basic features can be quantified.

Although FIG. 3 shows an approximated ellipse which is set based on a minor axis 107 and a length 110 from a center to a blunt end, the setting procedure of the approximated ellipse is not limited thereto. For example, the approximated ellipse can be set based on the minor axis 107 of the egg and the length 109 from a center to a narrow end of the egg, or base on a major axis 106 of the egg and the minor axis 107 of the egg. In addition, the approximated ellipse can be set by using a tangent line to a contour 101 of the wide side of the egg. That is, the approximated ellipse means an ellipse which is arbitrarily set based on parameters which can be extracted from a contour 101 of the egg.

Next, an apparatus for determining the sex in this embodiment will be schematically described with reference to FIGS. 4A and 4B, and FIG. 5. Each of FIGS. 4A and 4B shows an egg stand 401 for taking an image of a whole contour of an egg without using any other materials and for taking a high-contrast image, and also shows an egg 405 which is placed in a horizontal position on the egg stand 401. A hole 402 whose figure is similar to the egg is bored into the egg stand 401 and a slant face 403 which is smaller than the size of the egg by 10 to 15% is formed at an edge of the hole 402 such that the egg can be properly kept in a horizontal position.

A surface 404 is given a black mirror finish for obtaining a high contrast image. Firstly, when the surface is given a mirror finish, an incident light from a light source is reflected off a surface 404 of the egg stand 401, but there is an advantage that thus reflected light travels in a direction perpendicular to the egg stand 401 with an extremely low probability based on the principle of an incident angle and a reflection angle. In addition, if the surface is given a black mirror finish, an optical sensitivity of a camera is decreased because the surface 404 of the egg stand 401 is black, even if a certain amount of the reflected light travels in a direction perpendicular to the egg stand 401. Therefore, it becomes possible to minimize the reflected light which travels in the direction perpendicular to the egg stand 401 to a substantially negligible level. In this way, when the surface 404 of the egg stand is given a black mirror finish, it becomes possible to obtain a high-resolution image of a contour of an egg by enhancing the contrast between the egg 405 and the egg stand 401.

Figure 5A:
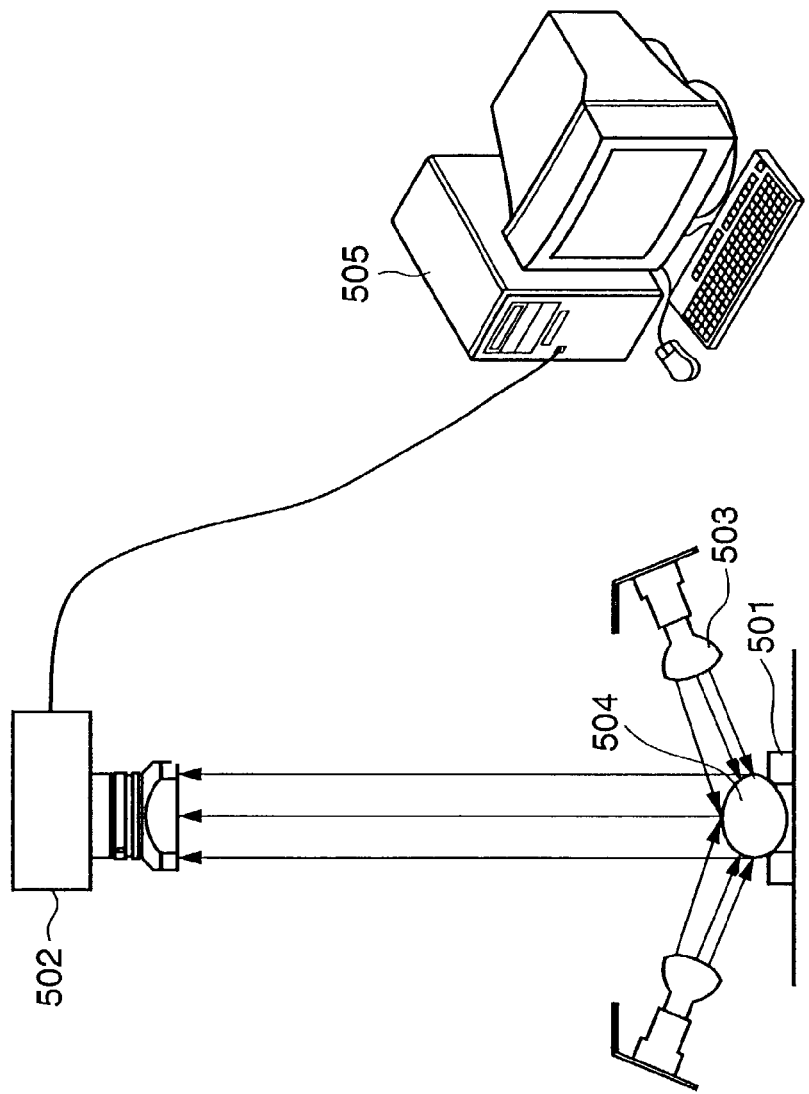
FIG. 5A is a diagram showing a configuration of an apparatus for practicing a method of the sex determination according to the present invention.

Next, FIG. 5A shows a configuration of an apparatus for extracting features or determining the sex by taking an image of an egg and processing the image data. An egg 504 is horizontally placed on an egg stand 501, and an image of the egg 504 is taken by a camera 502 which is located directly above the egg and in a direction perpendicular to the surface of the egg stand. As the camera 502, a still digital camera, a video camera or the like which uses, for example, a CCD as an image pickup device can be used. The egg 504 is uniformly illuminated by light from each lighting fixture 503. Each of the lighting fixtures 503 are disposed along a contour of the egg 504 as shown in FIG. 5B such that an appropriate contrast can be obtained and an image taken by the camera is not affected by incident light from any other portions.

The lighting fixtures 503 are provided such that an egg 504 is illuminated by the lighting fixtures 503 at an slightly upward angle to a horizontal direction and not at a right angle to a horizontal direction (only two lighting fixtures are described in FIG. 5A for simplicity). Consequently, even a lower portion of an contour of the egg 504 is sufficiently illuminated by these lighting fixtures 503, so that a side surface of the contour can be detected. Since a surface 404 of the egg stand 501 is given a black mirror finish as described above, light 506 projected from a lighting fixture 503 at a slightly upward angle is reflected off a surface 404 of the egg stand, but thus reflected light travels in a direction perpendicular to the surface 404 with an extremely low probability based on the principle of an incident angle and a reflection angle. Nevertheless, there exists light which travels toward the camera in a direction perpendicular to the surface 404 of the egg stand even when the lighting fixtures 503 illuminate the egg at a slightly upward angle, because the surface of the egg 504 has microscopic asperities. In addition, since the egg 504 has energy of light such as white light or red light, the energy of light from the egg which arrives at the camera becomes larger compared with energy of light from the surface 404 of the egg stand. Consequently, a contrast between the egg and its background is greatly improved by adjusting an incident sensitivity of the camera, so that a contour of the egg is easily detected stably and precisely.

Also, the egg can be irradiated with laser light, instead of using the lighting fixtures 503. In addition, another technique, in which a backlight is mounted within an egg stand 501 and a contour of the egg is extracted by using the backlight, can also be utilized. An image taken by the camera 502 is transferred as digital data to a computer 505 used for analysis or determination.

FIG. 5C is a block diagram of a computer 505 shown in FIG. 5A. Reference numeral 510 denotes a CPU, which controls a whole apparatus by using programs and data stored in RAM 511 or ROM 512 and also performs processing for determining the sex of the egg. Reference numeral 511 denotes ROM which stores programs and data for controlling the whole apparatus. Reference numeral 512 denotes RAM, which provides a work area used by the CPU 510 for performing various processing and a VRAM area for storing display data to be displayed on a display 513.

Reference numeral 513 denotes a display for displaying display data stored in the VRAM area and this display is comprised of a CRT or a liquid crystal display. Reference numeral 514 is an interface for connecting the computer 505 with the above described imaging device 502.

Reference numeral 515 denotes an input such as a keyboard, a mouse, or other operator's consoles. Reference numeral 516 denotes a communication interface for connecting with a LAN or the Internet. Reference numeral 517 denotes an HDD, which functions as memory for storing image data acquired by the imaging device, measured data obtained form the above described image data, or the like.

[Procedure for Determining the Sex]

Figure 6:
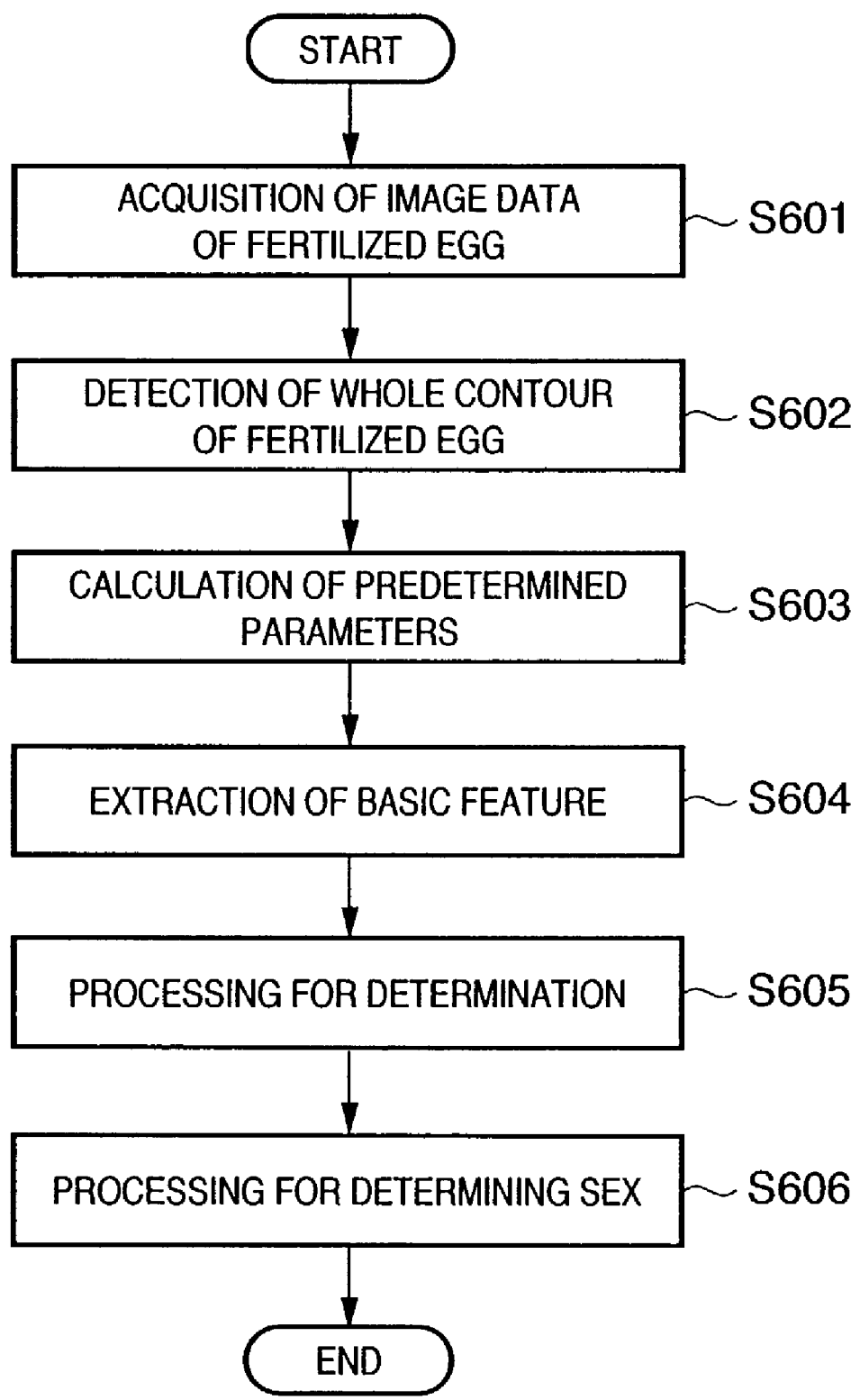
FIG. 6 is a flowchart showing a process for determining the sex of a fertilized egg according to the present invention.

Next, a procedure for determining the sex will be described. FIG. 6 is a flowchart of sex determination processing which is performed by an apparatus shown in FIG. 5. First, an image of an egg is taken by a camera 502 and is acquired by a computer 505 as image data (S601).

The above described acquired image data is processed by the computer 505. The image data acquired by the computer 505 at S601 is firstly stored within RAM 512. Next, a CPU 510 detects an edge by identifying a contrast between the image of the egg taken by the camera and the background thereof, and maps the detected edge as image data of the whole contour of the egg (S602). The whole contour herein means the whole contour of the egg which can be mapped as a two-dimensional image obtained by the camera 502 which is located directly above the egg 504, so that it does not mean the three-dimensional contour or a part of two-dimensional contour of the egg. Further, left and right edges and upper and lower edges on the mapped data are determined, and coordinates of an intersection point of two lines, that is, a line between an upper end and a lower end and a line between a blunt end and a narrow end are calculated. A length from the intersection point to a blunt end and a half of a distance between the upper end and the lower end are used as a long radius and a short radius respectively to make an approximated ellipse, and a center of this ellipse is matched to a center of the egg.

Subsequently, based on the obtained contour data, the CPU 510 determines a major axis, a minor axis, a center, and an area of the fertilized egg and also determines a major axis, a minor axis, an area and the like of the ellipse, all of which have already been described with reference to FIGS. 1 to 3, as parameters required for extracting the basic features, and then widths at arbitrary positions in a major axis direction of the egg to be required are calculated (S603). Then, the basic features developed on a contour shape of the fertilized egg are extracted (or quantified) by using numerical values of respective parameters obtained from the above described calculation and by combining these parameters (S604).

Next, processing for determining the sex is performed based on the basic features which are developed on the contour shape of the fertilized egg, the basic features being quantified at S604 (S605). Specifically, it is determined whether the basic features of the contour shape quantified at S604 reaches a level in which features of male eggs or female eggs are developed, based on the basic features which are quantified by using the predetermined parameters and threshold values which become references for determining the sex and are set for every basic feature.

For example, roundness at a blunt end is quantified, that is, a width at a position which is 90% of the whole length from the center to the blunt end of the egg is divided by a minor axis of the egg to give a value YR90. If the YR90 is larger compared with a threshold value Th1, a degree of "roundness at a blunt end" of the above described fertilized egg becomes sufficient for identifying the egg as a female egg, so that the egg is found to be a female egg.

On the other hand, if the above described YR90 is smaller than Th1, a degree of "roundness at a blunt end" of the above described fertilized egg is insufficient for identifying the egg as a female egg, so that the fertilized egg which is subjected to the above described processing cannot be identified as a female egg or a male egg, based on such features. However, even in this case, the sex determination can be performed based on other features.

A result of the determination processing at S605 is stored in an HDD 517 together with numerical values obtained by image data and image processing and is compiled into a database. Accuracy of the determination can be improved by continuously performing the determination processing and updating the database.

Then, the sex of the fertilized egg is determined in accordance with the determination result (S606). At this step, the determination result is displayed on the display 513, and then the fertilized egg may be mechanically or manually separated from other eggs in accordance with the displayed result.

The determination processing at S605 in FIG. 6 will be described in detail by bringing it into correspondence with the basic features of the egg.

[Female Feature—Roundness of Wide Side]

An egg whose degree of roundness of a wide side (at a blunt end) thereof is remarkable has a high possibility of being a female egg. An egg, having a wide side whose roundness is remarkable, is considered as an egg having a contour 101 whose curvature in the vicinity of the blunt end 102 is large. Based on this matter, a width at a position which is 90% of the whole length from the center to the blunt end of the egg is divided by a minor axis of the egg, for example. In this manner, the roundness of the wide side can be quantified (this numerical result is termed YR90) and can be defined by the following equation.

[Equation 1]

$$YR90 = Wh90/Ly$$

Figure 7:
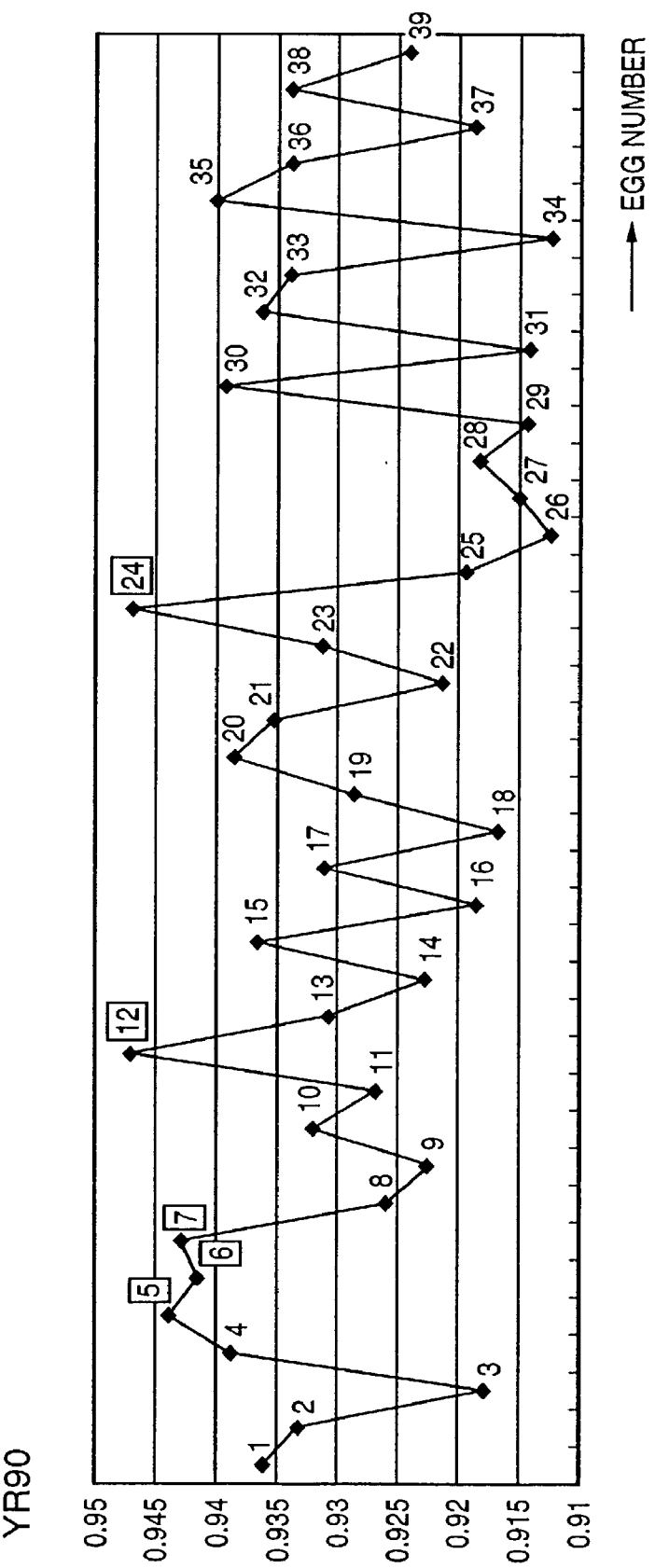
FIG. 7 is a graph on which a processing result is plotted, the processing result being obtained when an example of the sex determination processing based on roundness of a wide side of an egg is applied to each of 39 eggs.

FIG. 7 shows a result of determining the sex of an actual egg by means of this procedure. Thirty nine fertilized eggs of the white leghorn are prepared for this experiment, in which a shape of each egg is measured by the use of an apparatus shown in FIG. 5A and data required for the sex determination is extracted before hatching the egg and then the sex of the hatched hatchling is determined by hand. All of the eggs are numbered based on the result of the determination, and specifically, numbers from 1 to 24 represent female eggs and numbers from 25 to 39 represent male eggs.

In FIG. 7, YR90 values of five eggs which are numbered 5, 6, 7, 12, and 24 (corresponding to boxed numbers in this figure) are larger than YR90 values of male eggs, so that these five eggs can be identified as female eggs. Therefore, in a graph shown in FIG. 7, the five eggs numbered 5, 6, 7, 12, and 24 can be identified as female eggs provided that a threshold value (Th1) is set at 0.941.

In FIG. 7, five eggs out of twenty four eggs can be identified as female eggs. The sex of nineteen other eggs cannot be determined at this stage. However, the fertilized egg is a living matter and is shaped under the influence of nature. Therefore, the sex of some eggs cannot be determined even if they have common features. This is true for the human, because it can be recognized at a glance that some babies are females but other babies cannot be identified as females or males at a glance. Therefore, there is no need to identify all of the female eggs by the feature of "roundness of the wide side", but eggs which are undoubtedly female can be specified based on this feature. In addition, the threshold value which is set at this stage can be set as a value for specifying the eggs which are undoubtedly female.

Further, processing of the sex determination can be performed based on the result (R85) which is obtained by quantifying the bulge of the wide side based on the following equation.

[Equation 2]

$$R85 = Wh85/Ly$$

Wh85 in the above equation represents a length of a width 202 at a position which is 85% of the whole length from the center 108 to the blunt end 102 of the egg.

Figure 8:
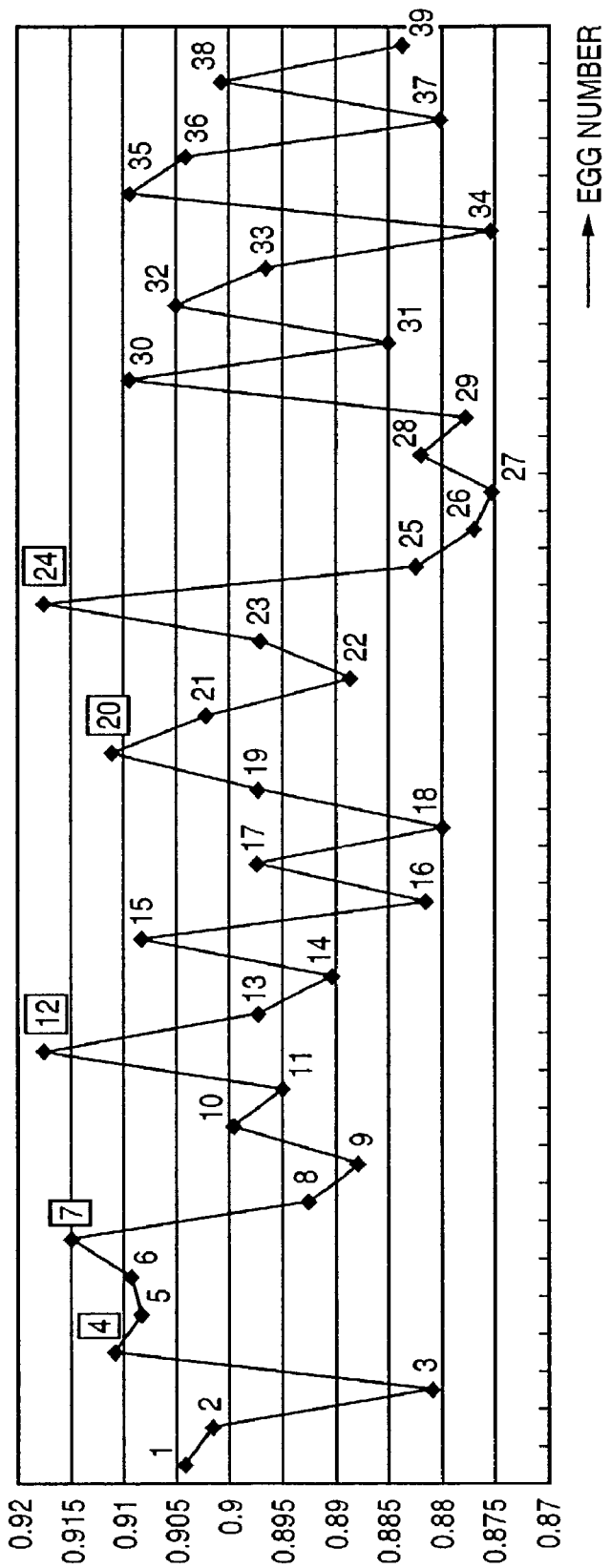
FIG. 8 is a graph on which a processing result is plotted, the processing result being obtained when an example of the sex determination processing based on roundness of a wide side of an egg is applied to each of 39 eggs.

FIG. 8 shows a result obtained by performing the sex determination on the above described 39 eggs, based on the bulge of the wide side derived from [Equation 2]. In this case, if a threshold value (Th2) is set at 0.91, four eggs numbered 4, 7, 12, 20, and 24 having R85 values larger than Th2 are identified as females, and other eggs are determined that they are not females, to say the least of it. In this manner, the sex of 39 eggs can be determined. When the bulge of the wide side is quantified, a differential value at an arbitrary position on a contour of the wide side is determined, then thus obtained differential value which is larger than the other differential values can be used as a feature of a female egg.

[Female Feature—Roundness of Narrow Side]

Figure 9:
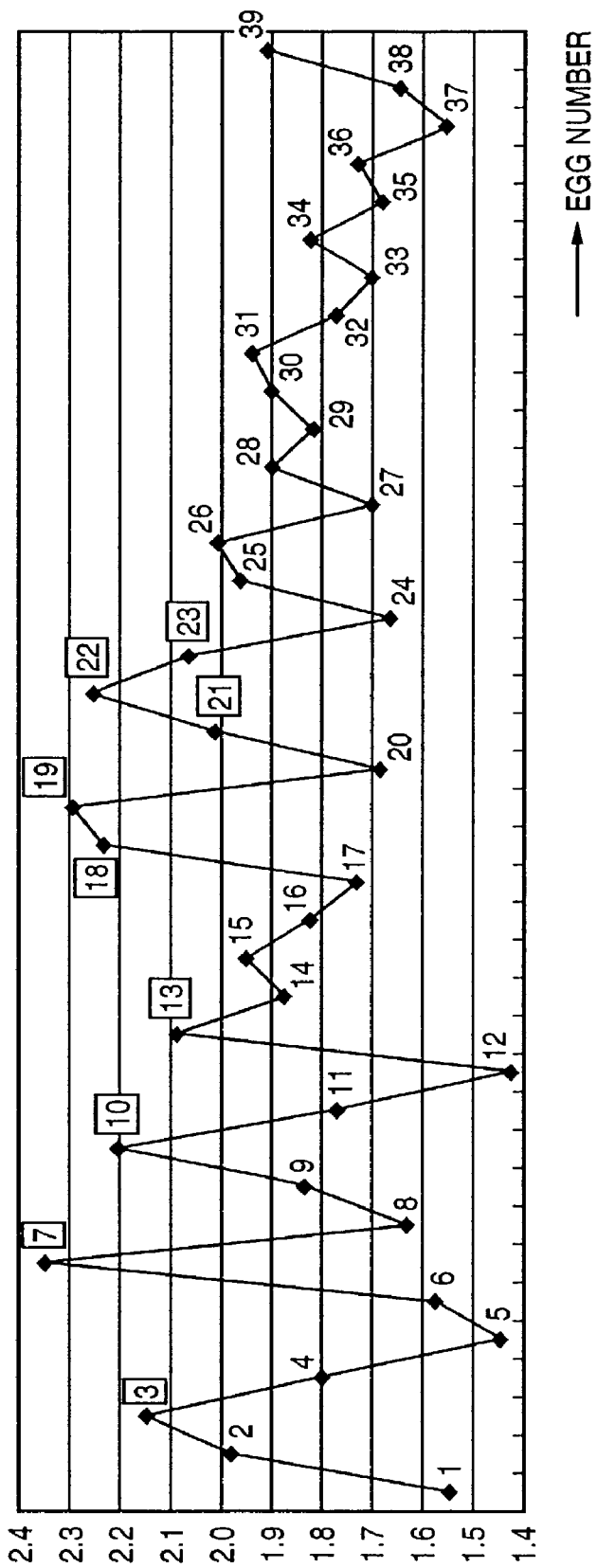
FIG. 9 is a graph on which a processing result is plotted, the processing result being obtained when an example of the sex determination processing based on roundness of a narrow side of an egg is applied to each of 39 eggs.

An egg whose degree of roundness of a narrow side thereof is remarkable has a high possibility of being a female egg. An egg, having a narrow side whose roundness is remarkable, is considered as an egg having a contour 101 whose curvature in the vicinity of the narrow end 103 is large. Specifically, the roundness of the narrow end can be clearly recognized by comparing the contour of the narrow side with its approximated ellipse. Describing this with reference to FIG. 3, reference numeral 301 denotes a length between a narrow end of the egg and a narrow end of the approximated ellipse. A width 303 represents a width of the approximated ellipse taken at a position in which a difference between a contour of a narrow end of the egg and a contour of a narrow end of the approximated ellipse is 90% of the length 301. Actually, in the sex determination, an inverse number (Gym) of the width 303 is used as a numerical value which represents the roundness of the narrow side of the egg. When the sex of the above described 39 eggs are determined based on the Gym values, the result as shown in FIG. 9 can be obtained. In this case, values on a longitudinal axis are features represented by the inverse numbers of the width 303 of the approximated ellipse shown in FIG. 3. If the threshold value (Th3) is set at 2.008, nine eggs numbered 3, 7, 10, 13, 18, 19, 21, 22, and 23 whose Gym values are larger than Th3 can be identified as female eggs.

[Female Feature—Restriction in Narrow Side]

A female hatchling is hatched from an egg whose wide side is bulged larger than a narrow side of this egg (an egg having a restricted portion in its narrow side). The restriction in the narrow side can be determined by a ratio of a width of the narrow side to a width of the wide side of the egg, and especially, the features of females can be sufficiently recognized by using a width in the vicinity of the tail portion. For example, a width 203 taken at a position being 50% of a whole length from a center to a blunt end is divided by a width 205 taken at a position being 85% of a whole length from a center to a narrow. In this manner, the restriction in the narrow side can be quantified (L85). The L85 is defined by the following equation.

[Equation 3]

$$L85=Wh50/Wt85$$

Figure 10:
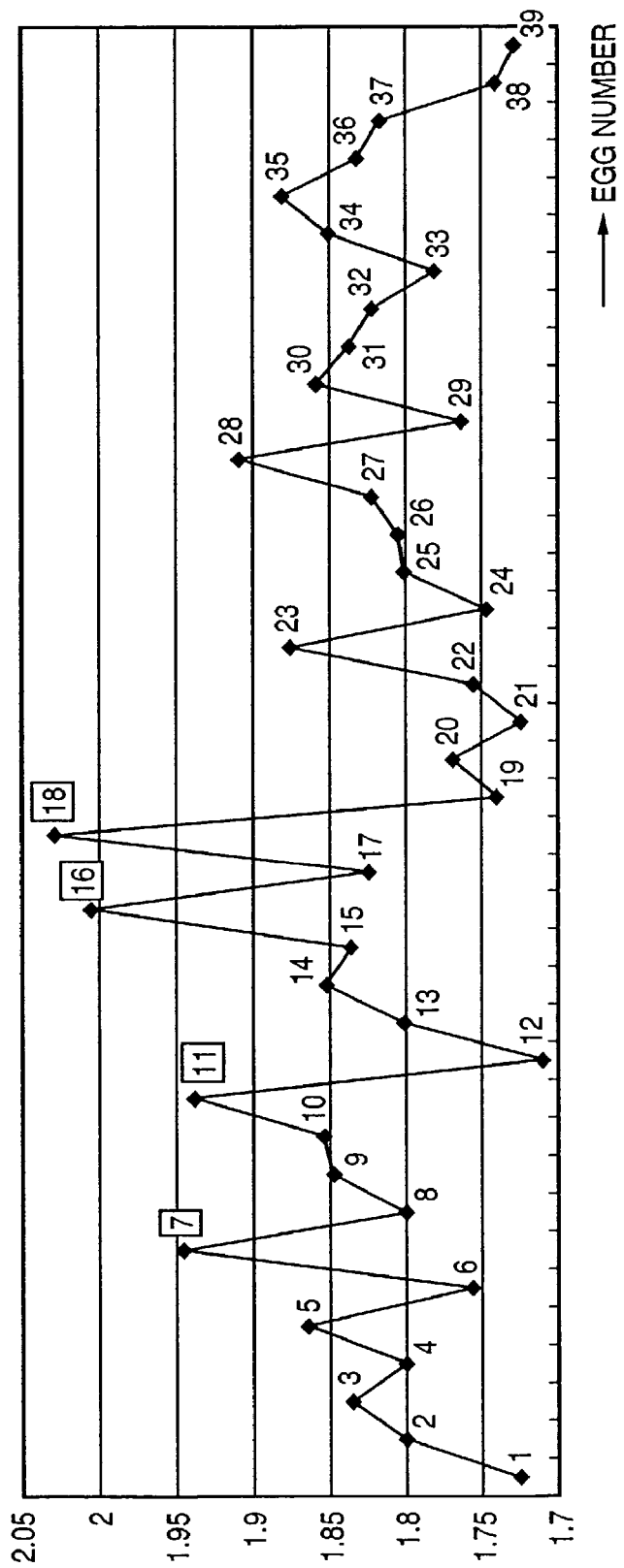
FIG. 10 is a graph on which a processing result is plotted, the processing result being obtained when an example of the sex determination processing based on a restriction in a narrow side of an egg is applied to each of 39 eggs.

FIG. 10 shows a result obtained by applying this determination procedure to the above described 39 eggs. In FIG. 10, if the threshold value (Th4) is set at 1.92, four eggs numbered 7, 11, 16, and 18 whose L85 values are larger than Th4 can be identified as female eggs. Instead of using the width 203 taken at the position being 50% of the whole length from the center to the blunt end, a minor axis 104 of the egg can also be used.

[Female Feature—Position of Center]

Since a position of a center can be determined by a ratio of a length of a narrow side to a major axis of the egg, a length of a narrow side 109 can be divided by a major axis 106 of the egg (this result is represented as GPT, which is defined by the following equation). It is also possible to divide a difference between an area of the egg and an area of an approximated ellipse by an area of the approximated ellipse.

[Equation 4]

$$GPT=Lxt/Lx$$

Figure 11:
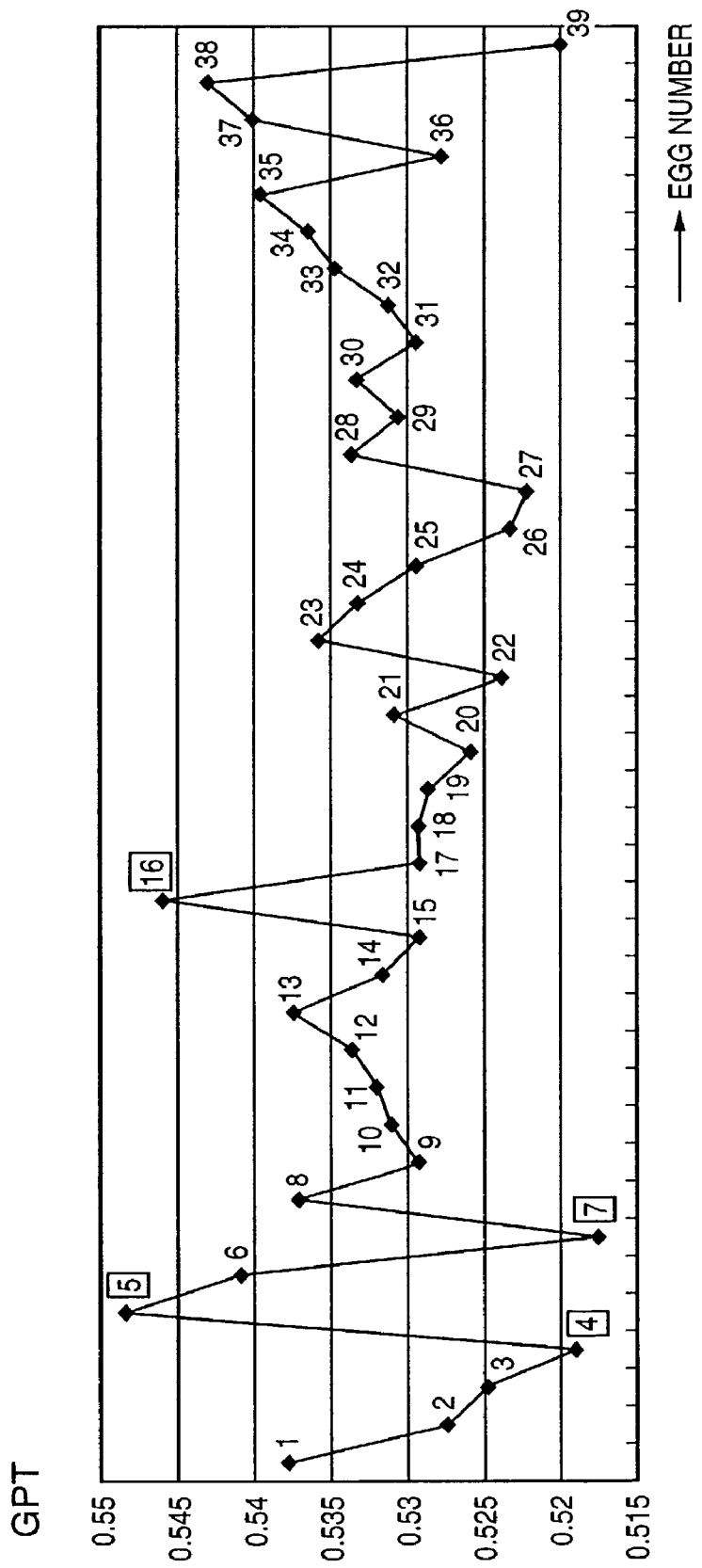
FIG. 11 is a graph on which a processing result is plotted, the processing result being obtained when an example of the sex determination processing based on position of a center of an egg is applied to each of 39 eggs.

FIG. 11 shows a result obtained by applying the sex determination technique based on the GPT values to the above described 39 eggs. In this case, female hatchlings (numbered 4, 5, 7, and 16) of the white leghorn are statistically hatched when the GPT value is larger than 0.54 (threshold value Th5A) or smaller than 0.52 (threshold value Th5B).

[Male Feature—Sharpness of Wide Side]

Sharpness of a wide side which is a feature of a male egg may be considered that a curvature of a contour 101 in the vicinity of a blunt end 102 is small. Based on this matter, for example, a minor axis of the egg is divided by a width taken at a position being 90% of a whole distance from a center to a blunt end. In this manner, the sharpness of the wide side of the egg can be quantified (GYR90). When parameters which are shown in FIG. 2 are used, the GYR90 is defined by the following equation.

[Equation 5]

$$GYR90=Ly/Wh90$$

Figure 12:
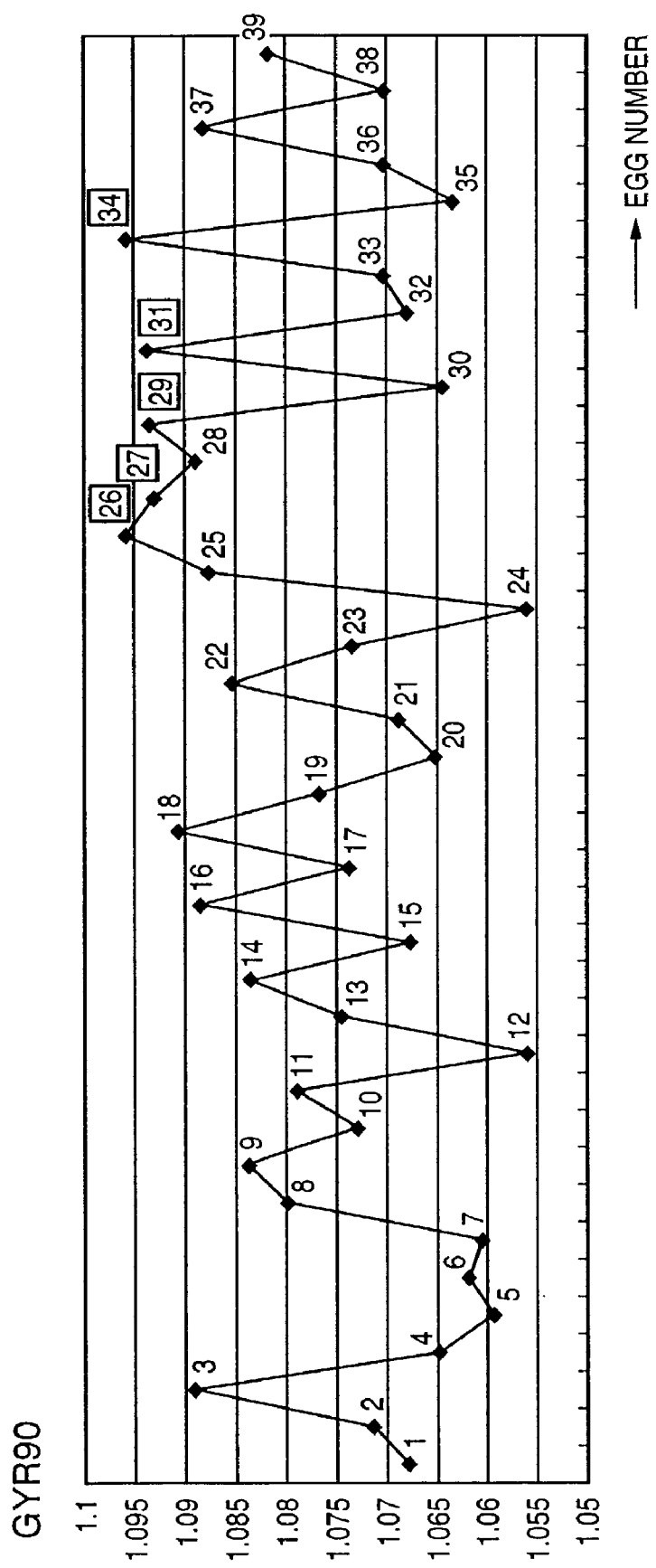
FIG. 12 is a graph on which a processing result is plotted, the processing result being obtained when an example of the sex determination processing based on sharpness of a wide side of an egg is applied to each of 39 eggs.

FIG. 12 shows a result obtained by applying this sex determination procedure based on the GYR90 values to the above described 39 eggs. In this case, if the threshold value (Th6) is set at 1.092, five eggs numbered 26, 27, 29, 31, and 34 whose GYR90 values are larger than Th6 can be identified as male eggs. In this manner, a degree of the sharpness of an end portion of the wide side can be characterized by the width of the end portion of the wide side. In addition, from line segments of the contour of the egg, the sharpness can be characterized by a modest slope of a contour of the wide side. Further, if a difference between an area surrounded by a contour of a wide side of the egg and an area of a wide side of the approximated ellipse becomes a large negative number, such an egg can be considered as a male egg.

[Male Feature—Fatness of Narrow Side]

An egg, having a narrow side whose fatness is remarkable, can be considered as an egg whose width in the vicinity of a narrow end of the egg is large. As a procedure for quantifying the fatness of the narrow side, a width 204 taken at a position being 90% of a whole length of the narrow side is divided by a minor diameter 107 of the egg, for example. A value obtained here (GR) is defined by the following equation.

[Equation 6]

$$GR=Wt90/Ly$$

Figure 13:
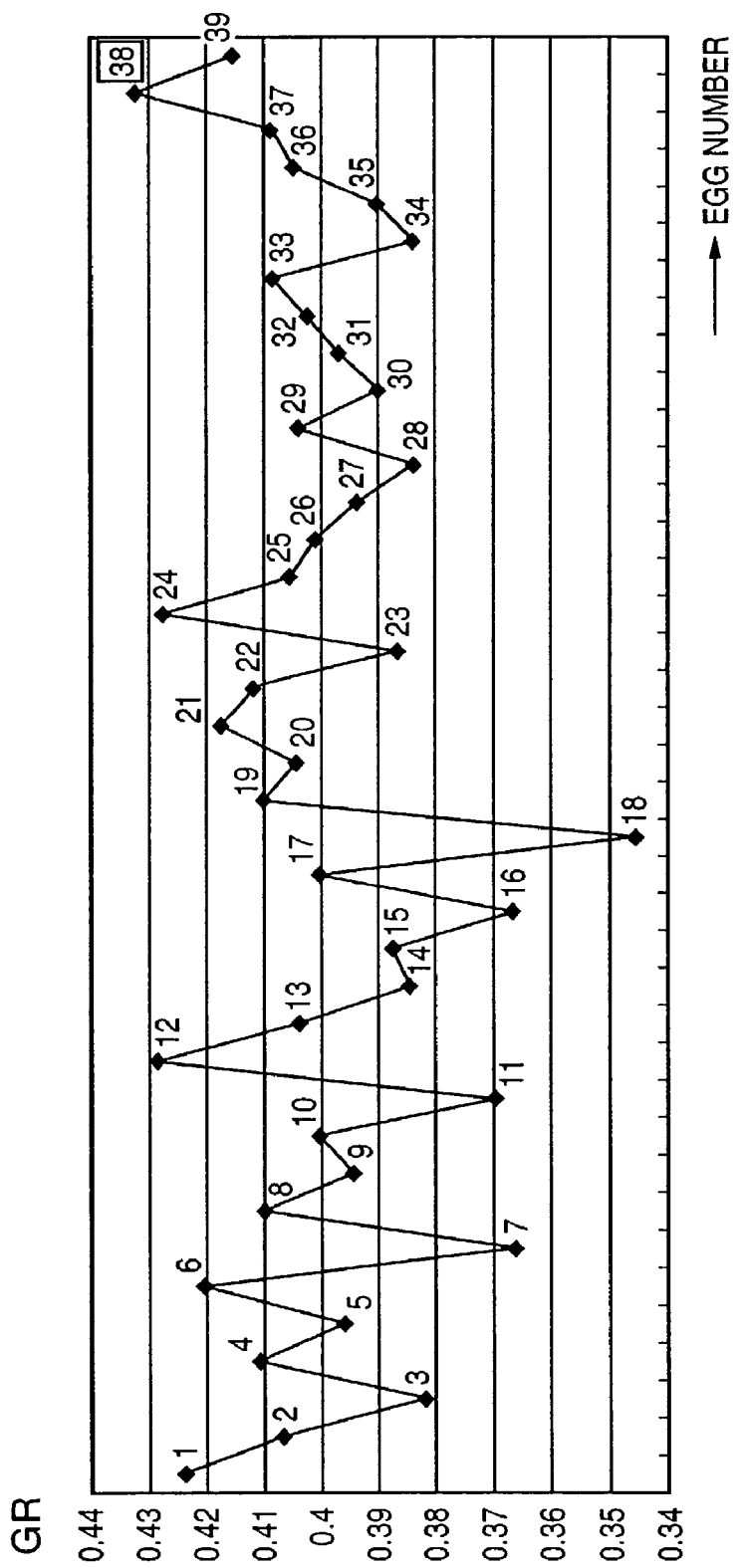
FIG. 13 is a graph on which a processing result is plotted, the processing result being obtained when an example of the sex determination processing based on sharpness of a narrow side of an egg is applied to each of 39 eggs.

FIG. 13 shows a result obtained by applying this sex determination procedure based on the GR values to the above described 39 eggs. In this case, if the threshold value (Th7) is set at 0.43, one egg numbered 38 whose GR value is larger than Th7 can be identified as male egg.

An egg whose narrow side is substantially fat can be considered as follows. That is, a width of an egg in the vicinity of a midpoint between a center and a narrow end at the narrow side is large, and more particularly, a difference between the width of the egg in the vicinity of the midpoint between the center and the narrow end and a maximum value of a width of the egg is small.

[Male Feature—Excessive Bulge of Wide Side]

Excessive bulge of a wide side can be considered as follows. That is, a width of an egg in the vicinity of a midpoint between a center and a blunt end at the wide side of the egg is large, and more particularly, a difference between the width of the egg in the vicinity of the midpoint between the center and the blunt end at the wide side of the egg and a maximum value of a width of the egg is small. Based on this matter, for example, a width taken at a position being 50% of a whole distance from a center to a blunt end is divided by a major axis of the egg. In this manner, a feature such as an excessive bulge of the wide side can be quantified (R50BX). When parameters which are shown in FIG. 2 are used, the R50BX is defined by the following equation.

[Equation 7]

$$R50BX = Wh50/Lx$$

Figure 14:
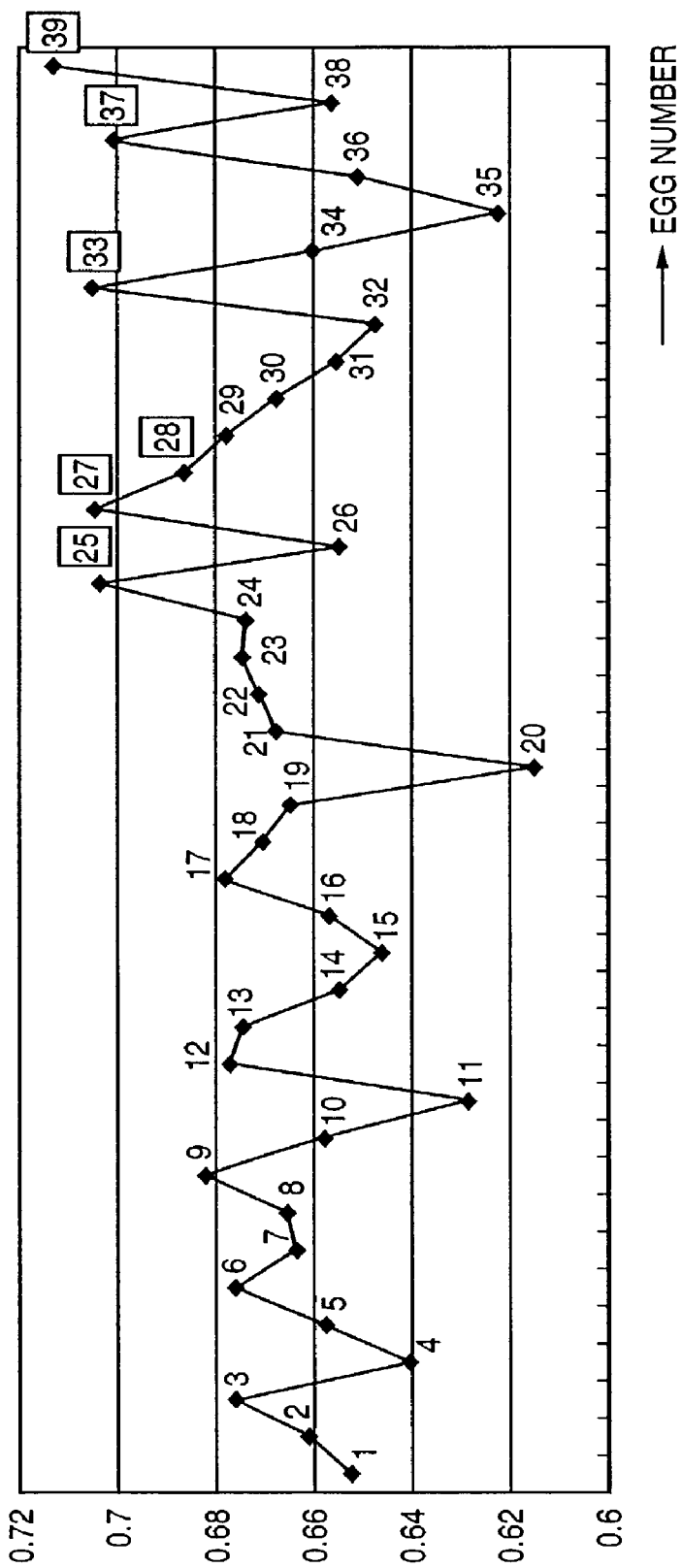
FIG. 14 is a graph on which a processing result is plotted, the processing result being obtained when an example of the sex determination processing based on a bulge of a wide side of an egg is applied to each of 39 eggs.

FIG. 14 shows a result obtained by applying this sex determination procedure based on the R50BX values to the above described 39 eggs. In this case, if the threshold value (Th8) is set at 0.684, six eggs numbered 25, 27, 28, 33, 37, and 39 whose R50BX values are larger than Th8 can be identified as male eggs. In addition, a quotient which is obtained by dividing a width taken at a position being 50% of a whole distance between a center and a blunt end by a short radius of an approximated ellipse or a minor axis of the egg can be used. Further, if a difference between an area surrounded by a contour of a wide side of the egg and an area half the size of the approximated ellipse becomes a large positive number, such an egg can be considered as a male egg.

In addition, the bulge of the wide side can be quantified (DFH) by dividing a difference between an area of a wide side of the egg and an area of a wide side of the approximated ellipse by an area of a wide side of the approximated ellipse. The numerical result DFH is defined by the following equation.

[Equation 8]

$$DFH = (Sxh - Seh)/Seh$$

Figure 15:
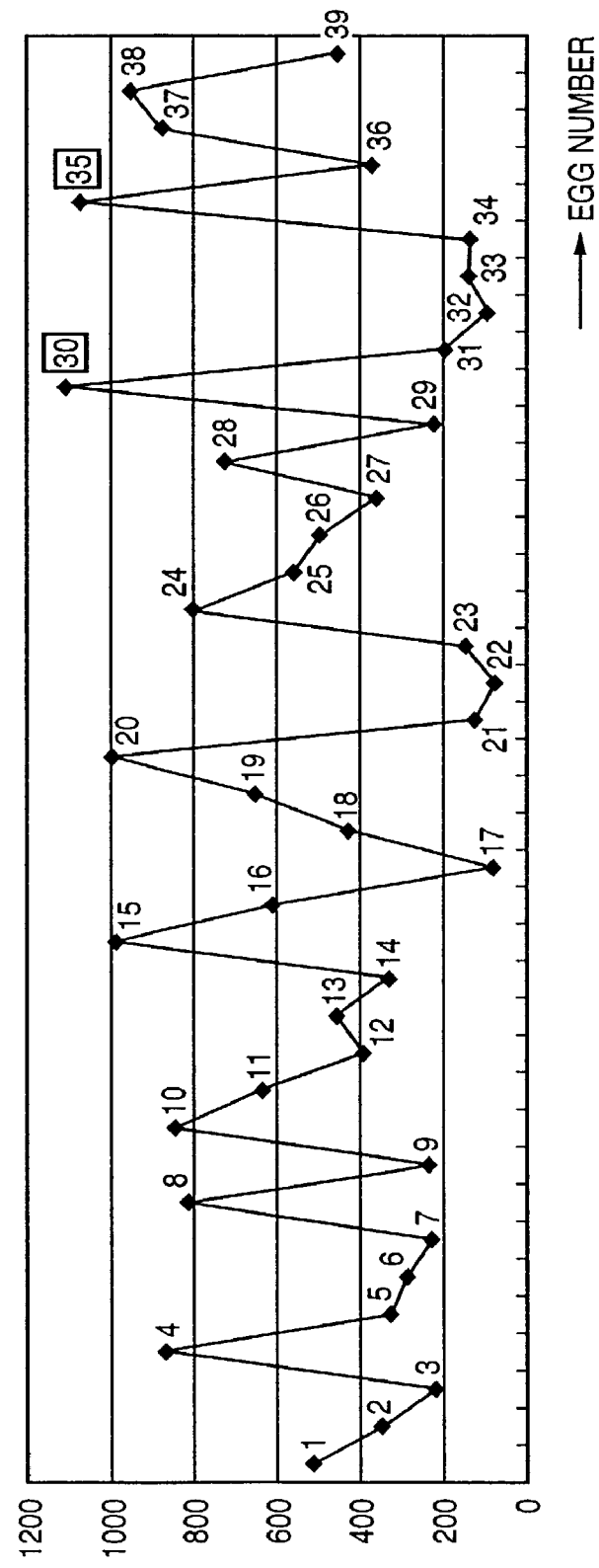
FIG. 15 is a graph on which a processing result is plotted, the processing result being obtained when an example of the sex determination processing based on a bulge of a wide side of an egg is applied to each of 39 eggs.

FIG. 15 shows a result obtained by applying this sex determination procedure based on the DFH values to the above described 39 eggs. In this case, if the threshold value (Th9) is set at 1000, two eggs numbered 30 and 35 whose DFH values are larger than Th9 can be identified as male eggs. A contour of a wide side of either egg is larger than that of the approximated ellipse. Further, it can be considered that, if a quotient obtained by dividing an area of the egg by a major axis of the egg is large, such an egg has a large bulge portion. Thus, the above described matter can also be used as a feature of a male egg.

[Male Feature—Slimness]

Figure 16:
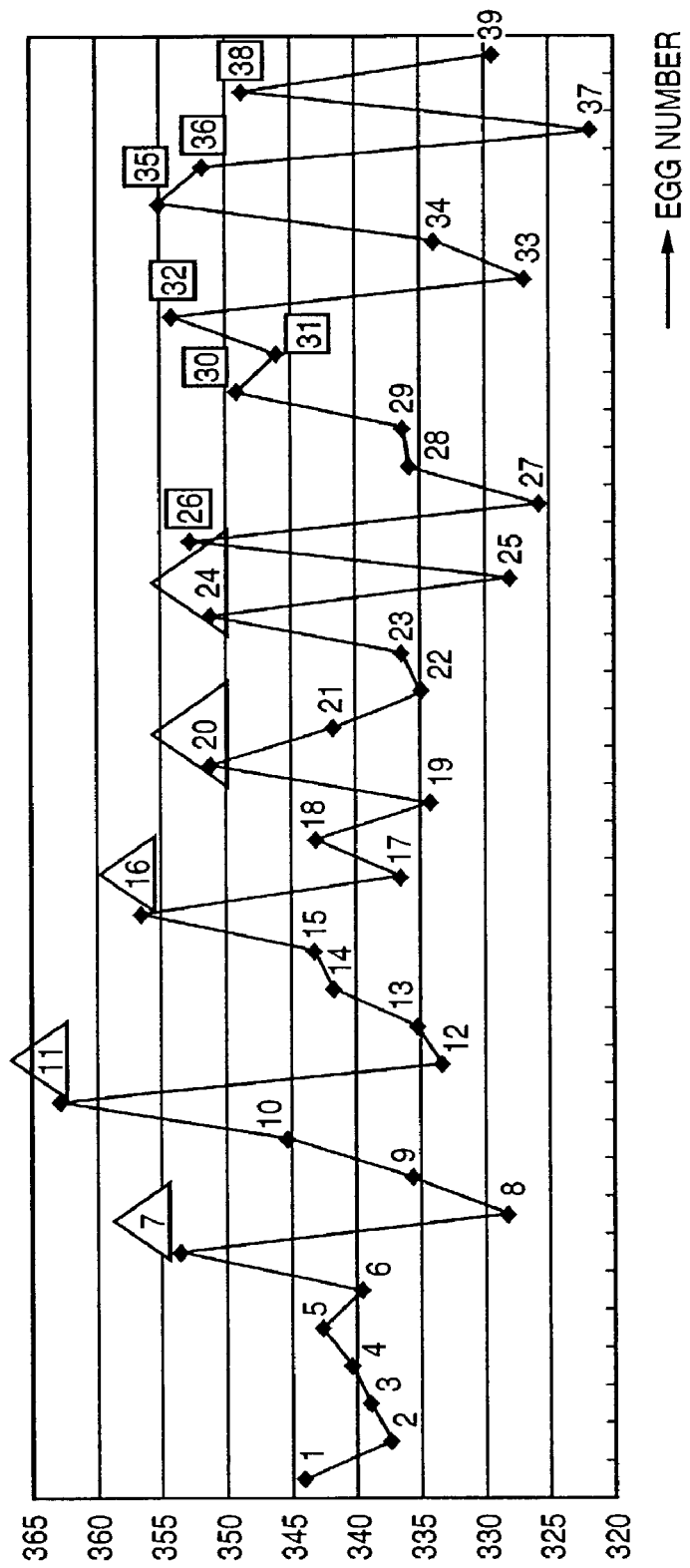
FIG. 16 is a graph on which a processing result is plotted, the processing result being obtained when an example of the sex determination processing based on slimness of an egg is applied to each of 39 eggs.

Slimness (or elongated shape) of an egg can be considered as follows. That is, a minor axis 107 of the egg is shorter relative to a contour 101 of the egg. Then, FIG. 16 shows a result of the sex determination based on the DSY values, the DSY values being obtained by the following equation. In other words, an area surrounded by a contour of the egg is divided by a minor axis of the egg to obtain the DSY value.

[Equation 9]

$$DSY = Sx/Ly$$

In FIG. 16, although DSY values of female eggs 7, 11, 16, 20, and 24 (corresponding to numbers enclosed in triangles in this figure) are larger than DSY values of male eggs, such a significant feature of the female egg may be previously eliminated from the measurement result. After eliminating the feature of female eggs, the threshold value (Th10) is set at 345.5. Thus, it becomes possible that eggs numbered 26, 30, 31, 32, 35, 36, and 38 whose DSY values are larger than Th10 are identified as male eggs. When other samples, except the above described 39 eggs used for this embodiment, were subjected to the sex determination based on this feature, male eggs could be identified independently.

The above described technique for quantifying the basic features using predetermined parameters, the basic features being developed on a contour on which the sex of the fertilized egg is reflected, are described only for purpose of illustration of this embodiment. Therefore, extracting a certain basic feature by using a predetermined parameter without being limited to the above description and quantifying the extracted basic feature are only exertion of ability of those skilled in the art. Therefore, the resultant parameters and numerical values as well as the sex determination technique which uses such parameters and numerical values are apparently included within a technical scope of the present invention.

[Example of Sex Determination Based on the Combination of a Plurality of Determination Processing]

Basic features of female or male eggs are extracted by combining parameters which can be obtained from a contour of the egg. However, as for the respective basic features, it is difficult to cover all of the eggs having complicated shapes. For example, even in the case of female eggs, roundness at narrow ends of some eggs are remarkable or restriction in narrow sides of some eggs are remarkable. In this way, the development of the basic features of female eggs and male eggs depends on a variety of eggs, parent chickens, and circumstances where the eggs are hatched. Therefore, a high rate of sex determination can be obtained by combining these basic features and then incorporating the combined features to a program which sequentially performs the sex determination processing following the order of priority.

FIG. 18 is a list representing a result obtained by determining the sex of eggs by applying each determination processing described above. In FIG. 18, a circle in each of determination processing GYR90 to DSY represents that an egg is identified as a male egg, but the determination whether an egg is a male egg or not cannot be accomplished by all of the determination processings. However, an accuracy of the determination can be dramatically improved by combining at least two determination processings.

Figure 17:
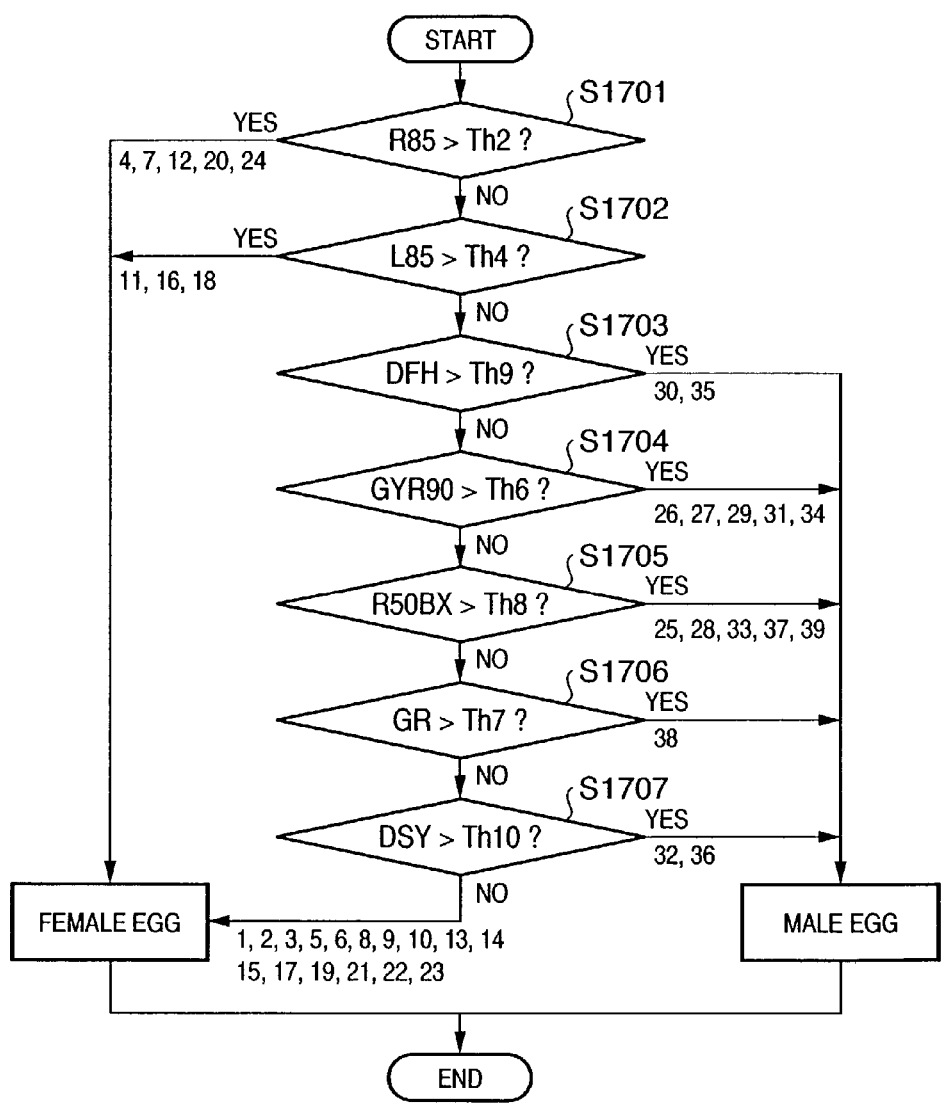
FIG. 17 is a flowchart corresponding to an example of the sex determination processing for determining the sex of an egg by applying more than one determination processing according to an embodiment of the present invention.

Then, as for the above described 39 eggs, a method for determining the sex of all of the 39 eggs by combining the determination processings YR90 through DSY will be described. FIG. 17 shows an example of a flowchart of this processing. FIG. 17 shows an example of a combination of the determination processings only for the purpose of illustrating this embodiment, so that a plurality of determination processings can be selected and combined with flexibility without being limited to the determination processing as adopted herein. For example, the determination processings to be adopted can be selected and set their priority based on a variety of parent chickens, or alternatively, the determination processings to be combined or priority thereof can be changed based on the age in month.

The flowchart shown in FIG. 17 can also be considered as a determination processing performed at S605 in FIG. 6. In FIG. 17, a step S1701 is a step for determining the roundness of a blunt end based on R85, and an egg which satisfies R85>Th2 is identified as a female egg. Next, at a step S1702, the restriction in a narrow side is determined based on L85, and an egg which satisfies L85>Th4 is identified as a female egg. Next, at a step S1703, the excessive bulge of a wide side is determined based on DFH, and an egg which satisfies DFH>Th9 is identified as a male egg.

Next, at a step S1704, the sharpness of the wide side is determined based on GYR90, and an egg which satisfies GYR90>Th6 is identified as a male egg. At a step S1705, the bulge of the wide side is determined based on R50BX, and an egg which satisfies R50BX>Th8 is identified as a male egg. At a step S1706, the fatness of the narrow side is determined based on GR, and an egg which satisfies GR>Th7 is identified as a male egg.

Next, at a step S1707, the slimness of the egg is determined based on DSY, and an egg which satisfies DSY>Th10 is identified as a male egg. In this embodiment, female eggs which are hardly determined can be left by determining male eggs at a step S1707.

In this manner, the sex determination can be performed for all of the 39 eggs by combining the determination processings as described in this embodiment. Similarly, the sex determination can be properly performed even if various shapes of eggs are included in subjects of the sex determination.

As a pre-processing of the flowchart shown in FIG. 17, an egg which is larger with reference to a value of an area of an egg is previously eliminated as a female egg. Consequently, an accuracy of the sex determination in each determination processing can be improved.

Further, a storage medium or a record medium, on which a program code of software corresponding to a flowchart of the sex determination processing of eggs shown in FIG. 6 and FIG. 17 are recorded, are supplied to a system or an apparatus, and the program code stored in the storage medium is read out and executed by a computer (or CPU and MPU) of the system or the apparatus, and consequently, the determination processing is performed. In this case, the program code in itself which has been read out from the storage medium performs a function of the above described embodiment, so that the storage medium in which the program code is stored constitutes the present invention.

The threshold values described in the embodiment of the present invention are numerical values obtained as a result of measuring a lot of eggs, but are not limited to the numerical values described herein. The threshold values can be modified by further performing the measurements and then accumulating the measured data, for the purpose of providing a higher precision. That is, the new threshold values which are set based on the result obtained by performing the above described determination processing can be naturally applied to each embodiment described above. And, a method or an apparatus for determining the sex of the eggs which has been practiced by using the above described new threshold values is included within the technical scope of the present invention.

Terms and expressions used in this specification are only for the purpose of description and are not limited thereto, therefore, terms and expressions which are equivalent to the above described terms and expression are not intended to be excluded. Further, the present invention is not limited to the embodiments shown in the appended drawings, and various modifications can be made without departing from the technical scope of the present invention.

In the present invention, as described above, the sex determination is performed by using basic female or male features quantified which can be obtained from a whole contour of an individual egg by means of a computer system. Therefore, it becomes possible to provide a method or the like for determining the sex of fertilized eggs with a high precision and at a high speed, which has been difficult to achieve by the conventional techniques relying on a human visual inspection or shape references. In addition, it also become possible to perform the sex determination of fertilized egg without depending on the parent chickens, by using parameters such as an approximated ellipse or a contour of an egg including a length, a maximum width, and a center of the egg as well as using basic features for the sex determination obtained by combining the above described parameters as references in order to perform the sex determination.

Also, female or male features are even extracted by using a minute section of the contour of the egg, and the sex determination is performed based on the extracted features. Therefore, this sex determination can also be applied to a fertilized egg whose shape is complicated, even when the shape of the egg will be changed as a result of the improvement of the parent chicken.

In addition, since the present invention provides a method for determining the sex with a high precision, fertilized male eggs can be used for other purposes such as foods or vaccines without decreasing the productivity of female hatchlings. Thus, these techniques can be contributed to the effective use of resources.

Further, since a surface of an egg stand on which the fertilized egg is placed is given a black mirror finish, a high contrast image can be obtained when an image of the fertilized egg is taken and its image data are acquired. Therefore, an accuracy of the determination can be improved.

As many apparently widely different embodiments of the present invention can be made without departing from the spirit and scope thereof, it is to be understood that the invention is not limited to the specific embodiments thereof except as defined in the appended claims.

What is claimed is:

1. A method for determining the sex of a fertilized chicken egg, comprising:
    placing the fertilized chicken egg in a horizontal direction on an egg stand which is downwardly concave and has a substantially egg-shaped periphery, and which has a mirror-finished surface;
    taking an image of the whole fertilized chicken egg from directly above the fertilized chicken egg placed on the egg stand;
    inputting the taken image into an operation apparatus;
    generating two-dimensional contour image data of the fertilized chicken egg from the inputted image;
    extracting parameters which represent a shape of the fertilized chicken egg from the two-dimensional contour image data; and
    determining the sex of the fertilized chicken egg by using said extracted parameters.

2. A method for determining the sex of a fertilized chicken egg, comprising:
    obtaining two-dimensional contour image data of the fertilized chicken egg by taking an image of the fertilized chicken egg while the fertilized chicken egg is placed on an egg stand which has a mirror-finished surface;
    extracting: a length between a blunt end of the egg and a narrow end of the egg, a maximum width of the egg, a bulge at an arbitrary position on the contour, and a position of a center of a portion surrounded by the contour, from the two-dimensional contour image data of the fertilized chicken egg, as parameters representing the shape of said fertilized chicken egg;

and performing the sex determination by using a combination of said parameters.

3. A method for determining the sex of a fertilized chicken egg, comprising:
obtaining two-dimensional contour image data of the fertilized chicken egg by taking an image of the fertilized chicken egg while the fertilized chicken egg is placed on an egg stand which has a mirror-finished surface;
extracting parameters representing a shape of said fertilized chicken egg from the two-dimensional contour image data of the fertilized chicken egg;
determining the sex of a hatchling obtained by hatching said fertilized chicken egg;
obtaining threshold values against the extracted parameters for determining the sex of said egg based on the determined sex of the hatchling; and
determining the sex of another fertilized chicken egg by using said threshold value.

4. A mechod for determining the sex of a fertilized chicken egg based on a parameter representing a shape of said fertilized chicken egg, wherein the parameter is extracted from two-dimensional contour image data of said fertilized chicken egg obtained by taking an image of said fertilized chicken egg while the fertilized chicken egg is placed on an egg stand which has a mirror-finished surface, said method comprising:
determining a first line segment having a maximum value, from among a plurality of line segments each of which connects a point on a contour of a wide side of said fertilized chicken egg and a point on a contour of a narrow side of said fertilized chicken egg;
determining a second line segment having a maximum value, from among a plurality of line segments each of which is perpendicular to said first line segment and represents a width of said fertilized chicken egg between intersection points with a contour of said fertilized chicken egg;
extracting an intersection point of said first line segment and said second line segments; and
determining the sex of said fertilized chicken egg by using a position of said extracted intersection point as said parameter.

5. A method for determining the sex of a fertilized chicken egg based on parameters representing a shape of said fertilized chicken egg, wherein the parameters are extracted from two-dimensional contour image data of the fertilized chicken egg obtained by taking an image of said fertilized chicken egg while the fertilized chicken egg is placed on an egg stand which has a mirror-finished surface, said method comprising:
obtaining an ellipse as one of said parameters representing the shape of said fertilized chicken egg;
extracting one of: a major axis of said ellipse, a minor axis of said ellipse, and an error between a contour of said fertilized chicken egg and said ellipse, as another one of said parameters; and
performing the sex determination with at least one of said parameters.

6. A method for determining the sex of a fertilized chicken egg, comprising:
obtaining contour image data representing a contour of the fertilized chicken egg by taking an image of the fertilized chicken egg while the fertilized chicken egg is placed on an egg stand which has a mirror-finished surface;
from said contour image data, detecting a blunt end and a narrow end of said fertilized chicken egg, and detecting intersection points of said contour and a line representing a maximum width of said fertilized chicken egg, the line being perpendicular to a line connecting said blunt end and said narrow end;
setting an ellipse in which a length equal to half a length of a line segment connecting said detected intersection points is used as a short radius, and a length of a line segment connecting the blunt end and a midpoint of the line segment connecting said intersection points is used as a long radius; and
determining the sex of the fertilized chicken egg based on a shape of said ellipse, by using said set ellipse as a parameter representing the contour of said fertilized chicken egg.

7. A method for determining the sex of a fertilized chicken egg, comprising:
obtaining contour image data of the fertilized chicken egg by taking an image of the fertilized chicken egg while the fertilized chicken egg is placed on an egg stand which has a mirror-finished surface;
extracting a plurality of parameters representing a shape of said fertilized chicken egg from the contour image data of the fertilized chicken egg; and
determining the sex of said fertilized chicken egg by using new parameters obtained by normalizing one of said plurality of parameters by utilizing any of said plurality of parameters.

8. A method for determining the sex of a fertilized chicken egg, comprising:
obtaining two-dimensional contour image data of the fertilized chicken egg by taking an image of said fertilized chicken egg while the fertilized chicken egg is placed on an egg stand which has a mirror-finished surface;
extracting an area surrounded by a contour of said fertilized chicken egg and an area surrounded by an ellipse as a parameter representing the contour of said fertilized chicken egg, from said two-dimensional contour image; and
determining the sex of said fertilized chicken egg by using a degree of a difference between said area surrounded by the contour of said fertilized chicken egg and said area surrounded by said ellipse.

9. A method for determining the sex of a fertilized chicken egg, comprising:
obtaining two-dimensional contour image data by taking an image of said fertilized chicken egg while the fertilized chicken egg is placed on an egg stand which has a mirror-finished surface;
determining a ratio of a width at a predetermined position of a wide side of said fertilized chicken egg to a width at a predetermined position of a narrow side of said fertilized chicken egg based on said two-dimensional contour image data; and
determining the sex of said fertilized chicken egg by using said ratio.

10. A method for determining the sex of a fertilized chicken egg, comprising:
obtaining two-dimensional contour image data by taking an image of said fertilized chicken egg while the fertilized chicken egg is placed on an egg stand which has a mirror-finished surface;
quantifying a degree of roundness at a blunt end of said fertilized chicken egg based on said two-dimensional contour image data; and determining the sex of said fertilized chicken egg by using said quantified degree of roundness.

11. A method for determining the sex of a fertilized chicken egg, comprising:
   obtaining two-dimensional contour image data by taking an image of said fertilized chicken egg while the fertilized chicken egg is placed on an egg stand which has a mirror-finished surface;
   quantifying a degree of roundness at a narrow end of said fertilized chicken egg based on said two-dimensional contour image data; and
   determining the sex of said fertilized chicken egg by using said quantified degree of roundness.

12. A method for determining the sex of a fertilized chicken egg, comprising:
   obtaining two-dimensional contour image data by taking an image of said fertilized chicken egg placed on an egg stand which has a mirror-finished surface;
   taking a ratio of a width at a predetermined position of a wide side of said fertilized chicken egg to a maximum width of the egg and quantifying the ratio as a roundness of the wide side of said fertilized chicken egg based on said two-dimensional contour image data; and
   determining the sex of said fertilized chicken egg by using said quantified roundness of the wide side of said fertilized chicken egg.

13. A method for determining the sex of a fertilized chicken egg, comprising:
   obtaining two-dimensional contour image data by taking an image of said fertilized chicken egg while the fertilized chicken egg is placed on an egg stand which has a mirror-finished surface;
   determining a ratio of a width at a predetermined position of a wide side of said fertilized chicken egg to a width at a predetermined position of a narrow side of said fertilized chicken egg and quantifying the ratio as a degree of a bulge of the egg based on said two-dimensional contour image data; and
   determining the sex of said fertilized chicken egg by using said quantified degree of the bulge of the fertilized chicken egg.

14. A method for determining the sex of a fertilized chicken egg, comprising:
   obtaining two-dimensional contour image data by raking an image of said fertilized chicken egg while the fertilized chicken egg is placed on an egg stand which has a mirror-finished surface;
   dividing a width at a predetermined position of a wide side of said fertilized chicken egg by one of: a maximum length of the egg, a maximum width of the egg, and a short radius of an ellipse corresponding to a contour of the egg, and quantifying a quotient of the division as a degree of a bulge of the egg, based on said two-dimensional contour image data; and determining the sex of said fertilized chicken egg by using said quantified degree of the bulge of said fertilized chicken egg.

15. A method for determining the sex of a fertilized chicken egg, comprising:
   obtaining a two-dimensional contour image data by taking an image of said fertilized chicken egg while the fertilized chicken egg is placed on an egg stand which has a mirror-finished surface;
   dividing an area surrounded by a whole of a contour of said fertilized chicken egg by one of a maximum width of the egg and a maximum length of the egg, and quantifying a quotient of the division as a bulge of said fertilized chicken egg, based on said two-dimensional contour image data; and
   determining the sex of said fertilized chicken egg by using said quantified degree of the bulge of said fertilized chicken egg.

16. A method for determining the sex of a fertilized chicken egg, comprising:
   obtaining two-dimensional contour image data by taking an image of said fertilized chicken egg while the fertilized chicken egg is placed on an egg stand which has a mirror-finished surface;
   quantifying a differential at a position of a contour of a wide side of said fertilized chicken egg as a roundness of said fertilized chicken egg based on said two-dimensional contour image data; and
   determining the sex of said fertilized chicken egg by using said quantified roundness of said fertilized chicken egg.

17. A method for determining the sex of a fertilized chicken egg, based on parameters representing a shape of said fertilized chicken egg, wherein the parameters are extracted from two-dimensional contour image data of the fertilized chicken egg obtained by taking an image of said fertilized chicken egg while the fertilized chicken egg is placed on an egg stand which has a mirror-finished surface, said method comprising:
   determining a threshold with regard to features representing the sex of said fertilized chicken egg based on a boundary between a numerical value within a region in which female eggs and male eggs coexist and a numerical value within a region in which female eggs and male eggs do not co-exist; and
   determining the sex of said fertilized egg, based on the determined threshold, by identifying said fertilized chicken egg which has the numerical value within a region in which female eggs and male eggs do not co-exist as a male egg or female egg.

18. A method for determining the sex of a fertilized chicken egg, based on parameters representing a shape of said fertilized chicken egg, wherein the parameters are extracted from two-dimensional contour image data of the fertilized chicken egg obtained by taking an image of said fertilized chicken egg while the fertilized chicken egg is placed on an egg stand which has a mirror-finished surface, said method comprising:
   separating male eggs and females eggs from each other by using a feature which represents a statistically definite region in which female eggs and male eggs do not co-exist; and
   determining the sex of said fertilized chicken egg by using a feature which does not represent the definite region in which female eggs and male eggs do not co-exist.

19. A method for determining the sex of a fertilized chicken egg, comprising:
   extracting parameters representing a shape of said fertilized chicken egg based on image data obtained by taking an image of the fertilized chicken egg while the fertilized chicken egg is placed on an egg stand which has a mirror-finished surface;
   quantifying a feature, reflecting the sex of said fertilized chicken egg, of a shape of a contour of said fertilized chicken egg obtained from said image data by using at least one of said parameters; and
   determining the sex of said fertilized chicken egg based on said quantified feature.

20. The method for determining the sex of a fertilized chicken egg according to claim 19, wherein said feature includes at least one of: roundness at a blunt end, fatness of a narrow side, roundness at a narrow end, and restriction in the narrow side of said fertilized chicken egg.

21. The method for determining the sex of a fertilized chicken egg according to claim 19, wherein said feature is quantified by utilizing a width at a predetermined position on a contour of the fertilized chicken egg obtained from the contour of said fertilized chicken egg among said parameters.

22. The method for determining the sex of a fertilized chicken egg according to claims 19, wherein said feature is decided in association with an ellipse as a parameter representing the contour of said fertilized chicken egg.

23. A method for determining the sex of a fertilized chicken egg, comprising:
   obtaining two-dimensional contour image data by taking an image of said fertilized chicken egg while the fertilized chicken egg is placed on an egg stand which has a mirror-finished surface;
   extracting parameters representing a feature of a shape of said fertilized chicken egg based on said two-dimensional contour image data of the fertilized chicken egg;
   normalizing a first parameter among said parameters by utilizing a second parameter in order to obtain a third parameter; and
   determining the sex of said fertilized chicken egg based on the third parameter.

24. A method for determining the sex of a fertilized chicken egg, comprising:
   obtaining two dimensional contour image data of the fertilized chicken egg by taking an image of said fertilized chicken egg while the fertilized chicken egg is placed on an egg stand which has a mirror-finished surface;
   extracting contour data of the fertilized chicken egg from said image data;
   setting an ellipse based on said contour shape data;
   using said set ellipse as a parameter representing a contour of said fertilized chicken egg; and
   determining the sex of the fertilized chicken egg based on a shape of said ellipse.

25. A method for determining the sex of a fertilized chicken egg, comprising:
   extracting parameters representing a feature of a shape of said fertilized chicken egg from two-dimensional image data of the fertilized chicken egg obtained by taking an image of the fertilized chicken egg while the fertilized chicken egg is placed on an egg stand which has a mirror-finished surface;
   determining she sex of said fertilized chicken egg, based on roundness of a wide side of said fertilized chicken egg which is quantified by utilizing one of said parameters;
   determining the sex of said fertilized chicken egg, based on restriction in a narrow side of said fertilized chicken egg which is quantified by utilizing one of said parameters;
   determining the sex of said fertilized chicken egg, based on a degree of a bulge of the wide side of said fertilized chicken egg which is quantified by utilizing one of said parameters;
   determining the sex of said fertilized chicken egg, based on sharpness of the wide side of said fertilized chicken egg which is quantified by utilizing one of said parameters;
   determining the sex of said fertilized chicken egg, based on fatness of the narrow side of said fertilized chicken egg which is quantified by utilizing one of said parameters; and
   determining the sex of said fertilized chicken egg, based on slimness of said fertilized chicken egg which is quantified by utilizing one of said parameters.

26. A computer readable medium with a program stored thereon for causing a computer to execute a method for determining the sex of a fertilized chicken egg, said method comprising:
   extracting: a length between a blunt end of the egg and a narrow end of the egg, a maximum width of the egg, a bulge at an arbitrary position on a contour of the egg, and a position of a center of a portion surrounded by the contour, from two-dimensional contour image data of the fertilized chicken egg obtained by taking an image of said fertilized chicken egg while the fertilized chicken egg is placed on an egg stand which has a mirror-finished surface, as parameters representing a shape of said fertilized chicken egg; and
   performing the sex determination by using at least one of said parameters.

27. A computer readable medium with a program stored thereon for causing a computer to execute a method for determining the sex of a fertilized chicken egg based on parameters representing a shape of said fertilized chicken egg, wherein the parameters are extracted from two-dimensional contour image data of the fertilized chicken egg obtained by taking an image of said fertilized chicken egg while the fertilized chicken egg is placed on an egg stand which has a mirror-finished surface, said method comprising:
   separating male eggs and females eggs from each other by using a feature which represents a statistically definite region in which female eggs and male eggs do not co-exist; and
   determining the sex of said fertilized chicken egg by using a feature which does not represent the definite region in which female eggs and male eggs do not co-exist.

28. A computer readable medium with a program stored thereon for causing a computer to execute a method for determining the sex of a fertilized chicken egg, said method comprising:
   extracting parameters representing a shape of said fertilized chicken egg based on image data obtained by taking an image of the fertilized chicken egg while the fertilized chicken egg is placed on an egg stand which has a mirror-finished surface;
   quantifying a feature, reflecting the sex of said fertilized chicken egg, of a shape of a contour of said fertilized chicken egg obtained from said image data by using at least one of said parameters; and
   determining the sex of said fertilized chicken egg based on said quantified feature.

29. A computer readable medium with a program stored thereon for causing a computer to execute a method for determining the sex of a fertilized chicken egg, said method comprising:
   extracting parameters representing a feature of a shape of said fertilized chicken egg from two-dimensional image data of the fertilized chicken egg obtained by taking an image of the fertilized chicken egg while the fertilized chicken egg is placed on an egg stand which has a mirror-finished surface;

determining the sex of said fertilized chicken egg, based on roundness of a wide side of said fertilized chicken egg which is quantified by utilizing one of said parameters;

determining the sex of said fertilized chicken egg, based on restriction in a narrow side of said fertilized chicken egg which is quantified by utilizing one of said parameters;

determining the sex of said fertilized chicken egg, based on a degree of a bulge of the wide side of said fertilized chicken egg which is quantified by utilizing one of said parameters;

determining the sex of said fertilized chicken egg, based on sharpness of the wide side of said fertilized chicken egg which is quantified by utilizing one of said parameters;

determining the sex of said fertilized chicken egg, based on fatness of the narrow side of said fertilized chicken egg which is quantified by utilizing one of said parameters; and determining the sex of said fertilized chicken egg, based on slimness of said fertilized chicken egg which is quantified by utilizing one of said parameters.

30. An apparatus for determining the sex of a fertilized chicken egg, comprising:

a camera for taking an image of the fertilized chicken egg while the fertilized chicken egg is placed on an egg stand having a surface with a mirror finish;

converting means for converting said image of said fertilized chicken egg into two-dimensional contour image data;

extracting means for extracting parameters representing features of a surface shape of said fertilized chicken egg based on the contour image data of said fertilized chicken egg; and determination means for determining the sex of said fertilized chicken egg by using said parameters.

31. The apparatus for determining the sex according to claim 29, wherein the surface of said egg stand has a black mirror-finish.

32. The apparatus for determining the sex according to claim 29, further comprising an illumination unit for uniformly illuminating said fertilized chicken egg, wherein illumination light from said illumination unit is incident upon the surface of said egg stand, which is at a back side of said fertilized chicken egg, at an angle.

* * * * *

UNITED STATES PATENT AND TRADEMARK OFFICE
CERTIFICATE OF CORRECTION

PATENT NO. : 7,167,579 B2　　　　　　　　　　　　　　　　　　　　Page 1 of 1
APPLICATION NO. : 10/232180
DATED : January 23, 2007
INVENTOR(S) : Ryosuke Taniguchi It is certified that error appears in the above-identified patent and that said Letters Patent is hereby corrected as shown below:

Column 21, Line 44, (Claim 14, Line 3);

Change "raking" to --taking--.

Signed and Sealed this

Fourteenth Day of April, 2009

JOHN DOLL
*Acting Director of the United States Patent and Trademark Office*